(12) United States Patent
Britz-McKibbin

(10) Patent No.: US 10,768,183 B2
(45) Date of Patent: Sep. 8, 2020

(54) METABOLITE PANEL FOR IMPROVED SCREENING AND DIAGNOSTIC TESTING OF CYSTIC FIBROSIS

(71) Applicant: McMaster University, Hamilton (CA)

(72) Inventor: Philip Britz-McKibbin, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 55 days.

(21) Appl. No.: 15/361,216

(22) Filed: Nov. 25, 2016

(65) Prior Publication Data

US 2017/0199203 A1 Jul. 13, 2017

Related U.S. Application Data

(63) Continuation-in-part of application No. PCT/CA2015/000344, filed on May 26, 2015.

(60) Provisional application No. 62/002,993, filed on May 26, 2014.

(51) Int. Cl.
| | |
|---|---|
| *G01N 33/68* | (2006.01) |
| *G01N 33/50* | (2006.01) |
| *G01N 27/447* | (2006.01) |
| *A23L 33/10* | (2016.01) |
| *A23L 33/00* | (2016.01) |
| *G16H 50/20* | (2018.01) |
| *G16H 50/30* | (2018.01) |

(52) U.S. Cl.
CPC .......... *G01N 33/6893* (2013.01); *A23L 33/10* (2016.08); *A23L 33/40* (2016.08); *G01N 33/50* (2013.01); *G01N 33/6806* (2013.01); *G16H 50/20* (2018.01); *A23V 2002/00* (2013.01); *G01N 27/4473* (2013.01); *G01N 2560/00* (2013.01); *G01N 2570/00* (2013.01); *G01N 2800/382* (2013.01); *G01N 2800/52* (2013.01); *G16H 50/30* (2018.01)

(58) Field of Classification Search
None
See application file for complete search history.

(56) References Cited

FOREIGN PATENT DOCUMENTS

WO WO-2006060793 A3 * 12/2006 ......... G01N 33/6812

OTHER PUBLICATIONS

Flume, P.A. 2009. Pulmonary complications of cystic fibrosis. Respiratory Care 54(5): 618-625. specif. p. 618.*
Ramautar, R. et al. 2012. Enhancing the coverage of the urinary metabolome by sheathless capillary electrophoresis-mass spectrometry. Analytical Chemistry 84: 885-892. specif. pp. 885, 886, 887, 888, 890.*
Pullan, N.J. et al. May 1, 2013. Evaluation of an inductively coupled plasma mass spectrometry method for the analysis of sweat chloride and sodium for use in the diagnosis of cystic fibrosis. Annals of Clinical Biochemistry 50: 267-270. specif. p. 267.*
Sharer, N. et al. 1998. Mutations of the cystic fibrosis gene in patients with chronic pancreatitis. The New England Journal of Medicine 339(10): 645-652. specif. p. 645.*
Hadorn, B. et al. 1967. Free amino-acids in human sweat from different parts of the body. Nature 215: 416-417. specif. pp. 416, 417.*
Moran, A. et al. 2001. Protein metabolism in clinically stable adult cystic fibrosis patients with abnormal glucose tolerance. Diabetes 50: 1336-1343. specif. pp. 1336, 1337, 1340.*
Balch, W.E. et al. Application of Mass Spectrometry to Study Proteomics and Interactomics in Cystic Fibrosis. Ch. 14. In: Cystic Fibrosis: Diagnosis and Protocols. .Humana Press (publisher). Copyright 2011. Springer Sci.+Bus. Media, LLC. Magarida Amaral and Karl Kunzelmann (Eds). N.Y.. pp. 227-247; 227, 232, 233.*
Eng, W. et al. 2005. Sweat-testing in preterm and full-term infants less than 6 weeks of age. Pediatric Pulmonolgy 40: 64-67. specif. pp.*
International Preliminary Report on Patentability for PCT/CA2015/000344 dated Nov. 29, 2016.
Grasemann et al; "A randomized controlled trial of inhaled L-arginine in patients with cystic fibrosis" Journal of Cystic Fibrosis 12(5), pp. 468-474, Jan. 14, 2013.
Grasemann et al.: "Decreased systemic bioavailability of L-arginine in patients with cystic fibrosis" Respir Res 7(87), pp. 1-7, Jun. 9, 2006.
Clarke et al.; "Components of sweat: Cystic fibrosis of the pancreas compared with controls" JAMA, 101(4), pp. 490-500, 1961.

* cited by examiner

*Primary Examiner* — Thomas J. Visone
*Assistant Examiner* — Sharon M. Papciak
(74) *Attorney, Agent, or Firm* — Gowling WLG (Canada) LLP

(57) ABSTRACT

A method of diagnosing cystic fibrosis in a human subject is provided. The method includes the steps of: i) determining in a biological sample from the subject the level of one or more metabolic biomarkers; ii) comparing the level of the biomarker to a control level and determining the difference between the biomarker level and the control level; and iii) determining that the subject has cystic fibrosis or a related disorder when the difference in the level of the biomarker in the sample is statistically different from the control level.

14 Claims, 25 Drawing Sheets

A. Two-tiered Newborn Screening of CF

1. Immunoreactive trypsin (IRT) test
*Poor specificity/positive predictive value (PPV) = 3-10%*
2. DNA test: panel of mutations
*Large number of carriers/unknown or variable clinical history*

Table 1. Categories of positive CF screens[1]

| Category | IRT / DNA test | PPV (%) |
|---|---|---|
| A | IRT > 96th centile / 2 mutations | 100 |
| B | IRT > 96th centile / 1 mutation | 1.6 |
| C | IRT > 99.9th centile / no mutations | 0.1 |

B. Confirmatory Chloride Sweat Test

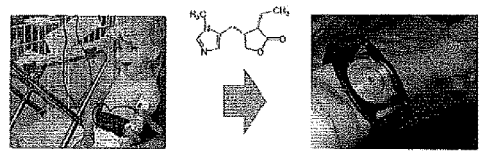

3. Sweat stimulation by pilocarpine iontophoresis
*Ambiguous sweat results for intermediate chloride*

Sweat collection in microbore tube

Chloridometer analysis

Table 2. Sweat chloride results[2]

| Cl⁻ (mM) | Result for CF |
|---|---|
| ≤ 29 | Negative |
| 30 – 59 | Inconclusive |
| ≥ 60 | Positive |

5-10% of screen-positives:
- Asymptomatic carrier
- CF-related disease
- CF pancreatic sufficient 85-90% screen-positives have normal sweat chloride (< 29 mM)

Figure 1.

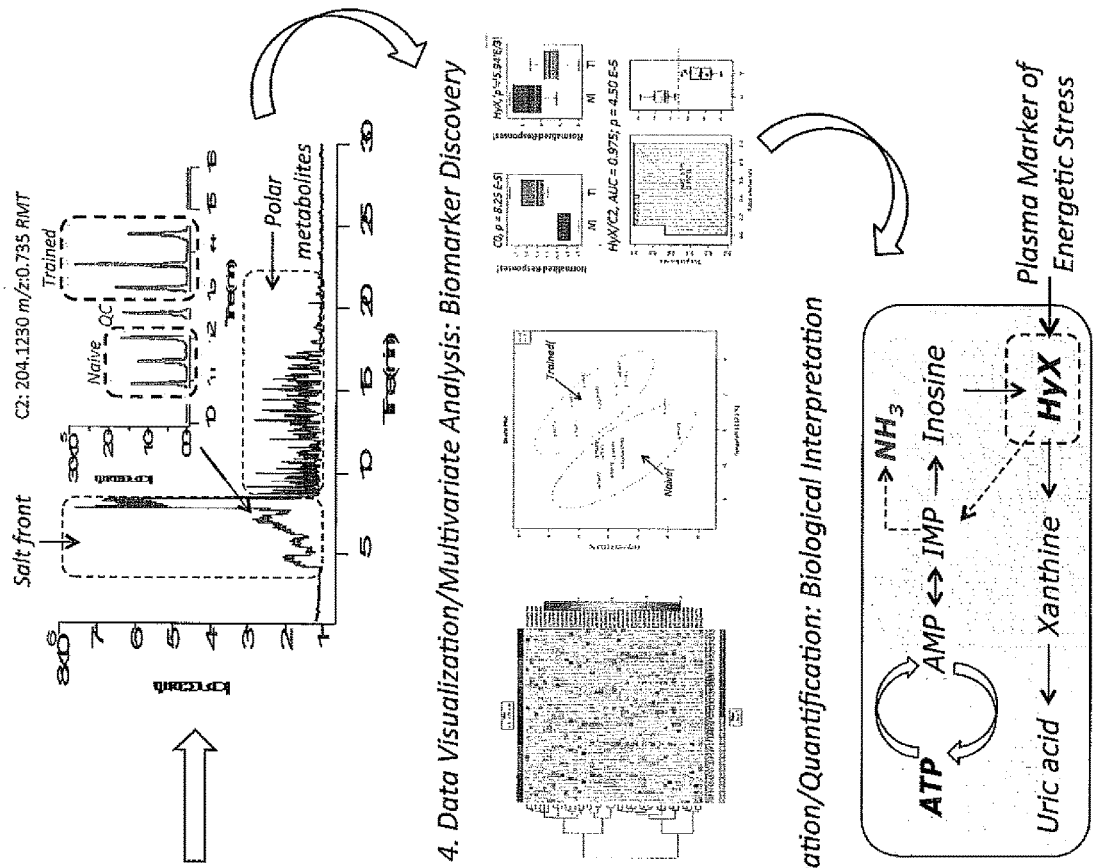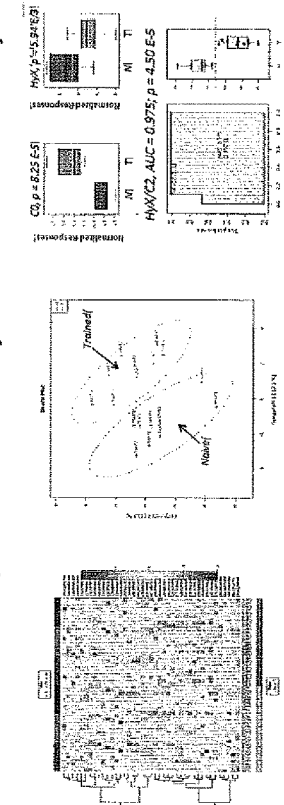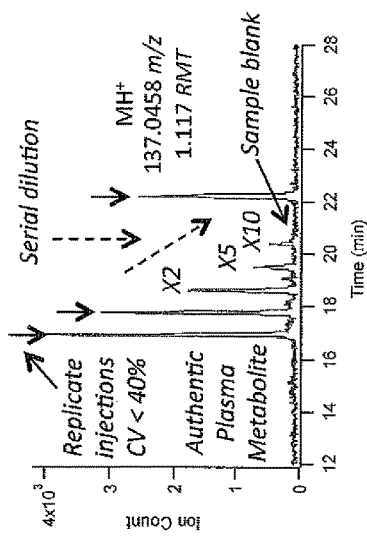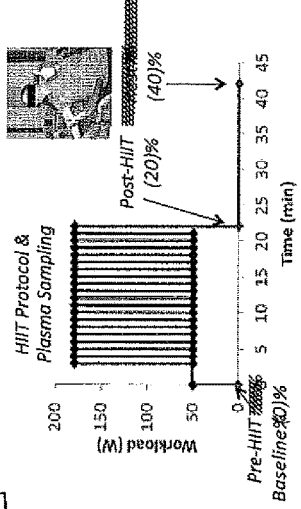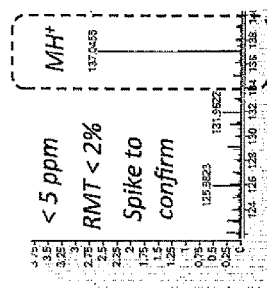
Figure 4.

Figure 6 continued
(b)
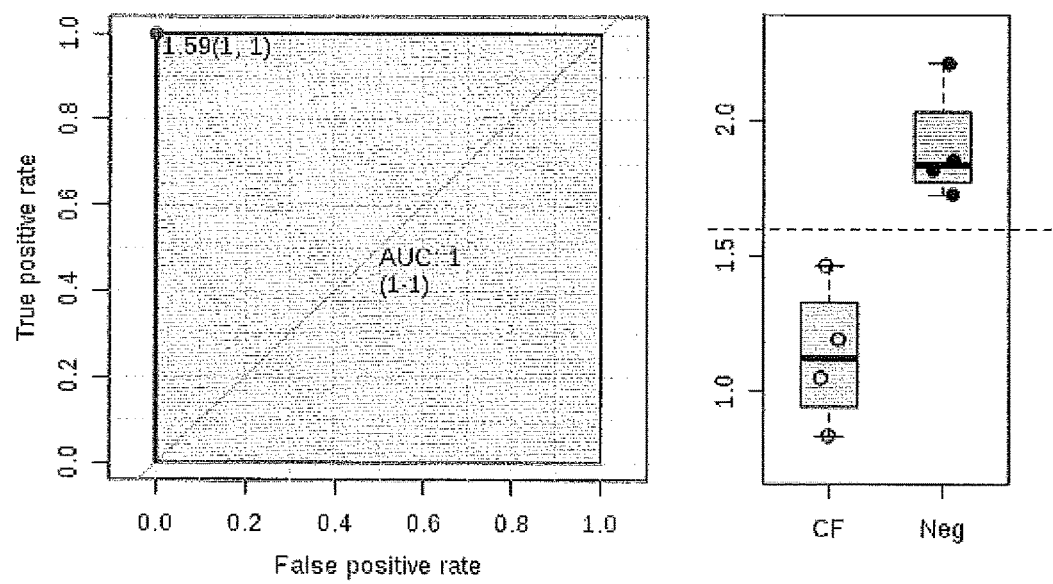
*Gln*   *AUC* = 1.00; *p* = 3.90 E-3
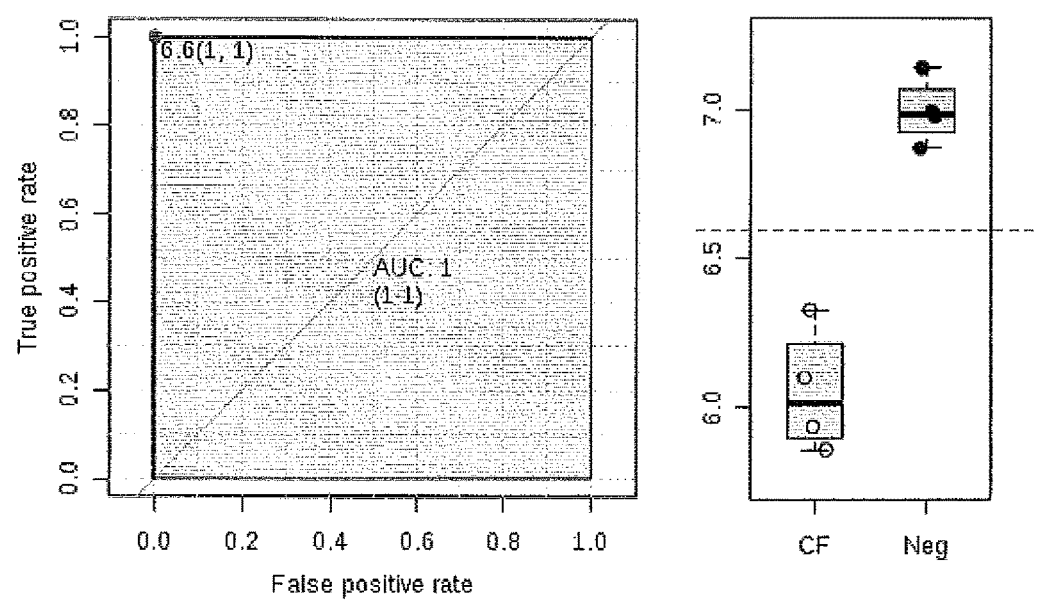
*Gln/C0*   *AUC* = 1.00; *p* = 2.03 E-4

Figure 7 continued
(b)
Unknown:
m/z: 238.095:1.108    AUC = 1.00; p = 6.20 E-6
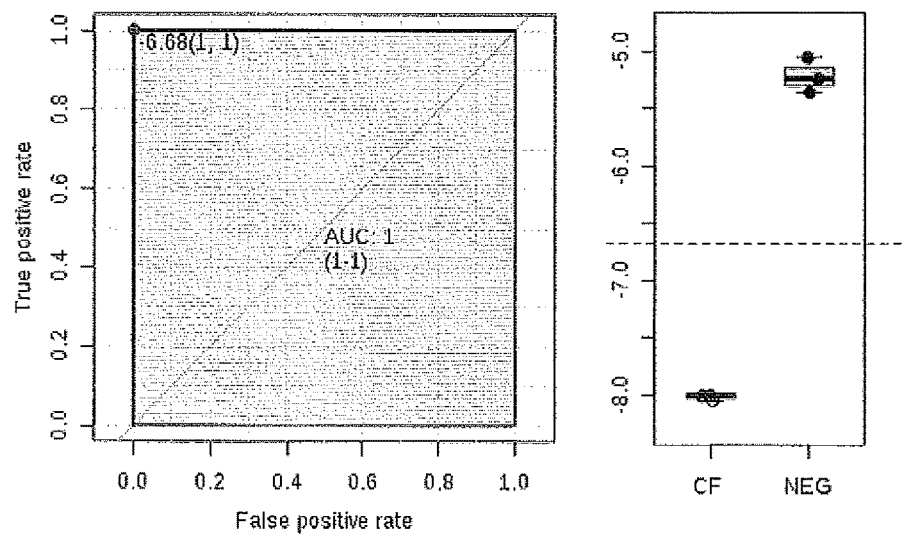
Cit/Unknown (238)    AUC = 1.00; p = 2.19 E-6
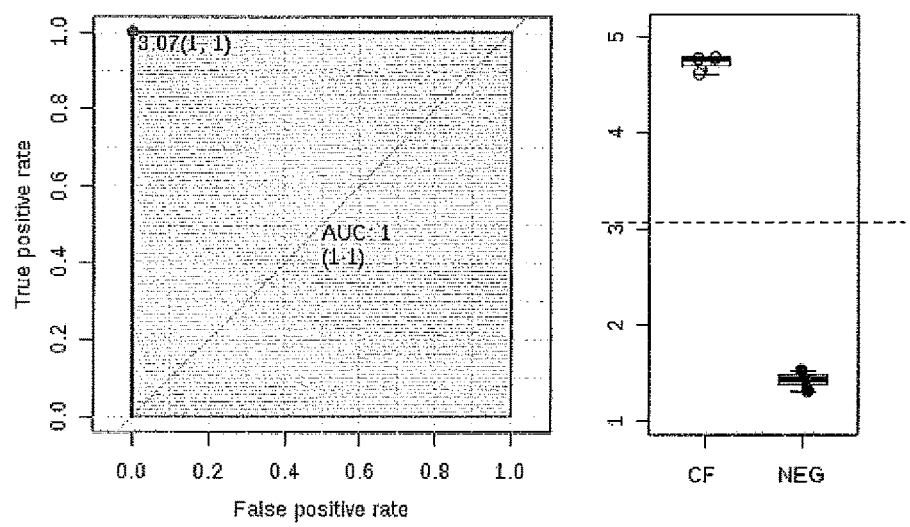

Figure 8.
1. Accurate Mass for Unknown Ion: 3 Empirical Formula
M = 237.0857; 3 formula candidates from MFG
| | ID | Formula | Isomers | Taut. Grps | dM(ppm) | |dM(ppm)| | Product | Precur. | Overall |
|---|---|---|---|---|---|---|---|---|---|
| 1 | 1 | C9H11N6O3 | 229 | 145 | -2.0 | 2.0 | 100 | 99 | 99 |
| 2 | 2 | C8H15NO7 | 87 | 42 | -3.7 | 3.7 | 100 | 97 | 97 |
| 3 | 3 | C9H19NO2S2 | 16 | 13 | 0.0 | 0.0 | 36 | 100 | 88 |
2. Extracted ion electropherogram: DBS extract spike
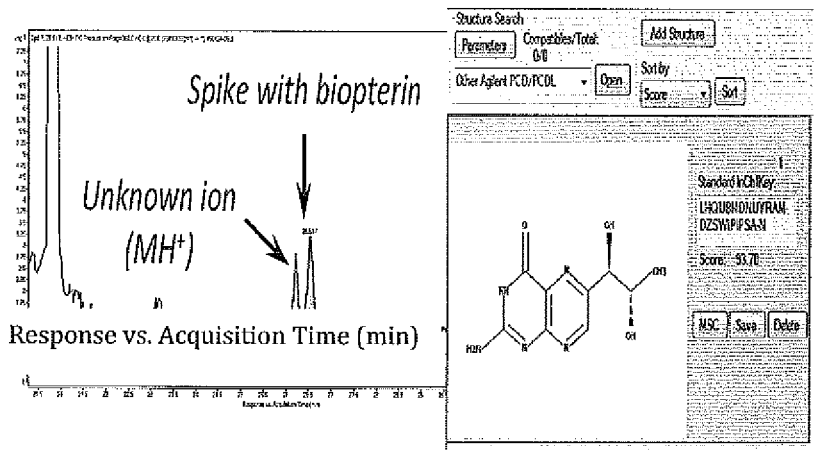
3. MS/MS Spectra: Product Ion Scan (Q-TOF)
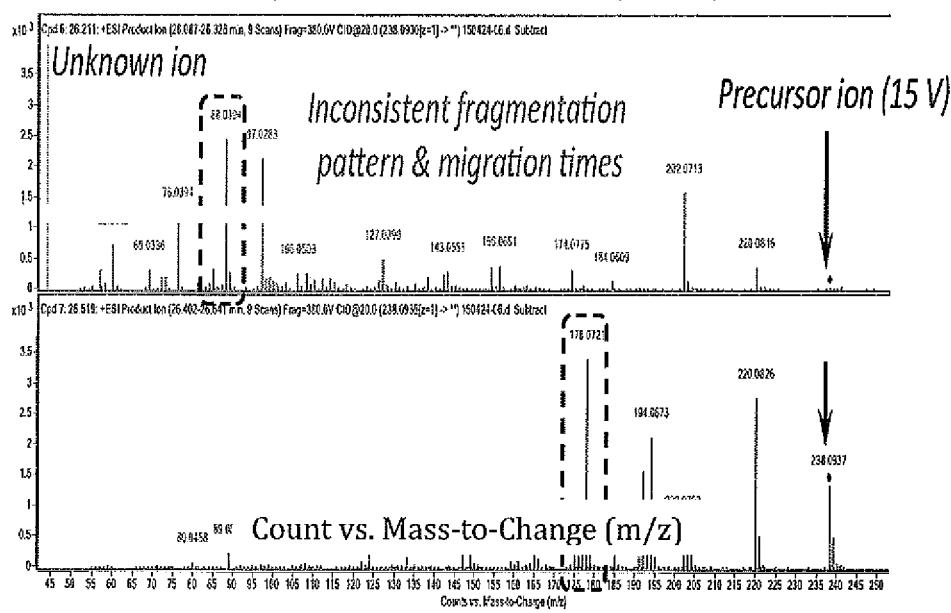
Count vs. Mass-to-Change (m/z)

(a)

(b)

(a)

(c)

Pilocarpine          Pilocarpic acid

Figure 15.
(a)
| m/z:RMT | Metabolite ID | p-value | Effect size | FC |
|---|---|---|---|---|
| 225.1245:0.777:n | Pilocarpic acid | 1.70E-06 | 0.54 | 0.39 |
| 133.0608:0.912:p | Asparagine | 5.22E-05 | 0.47 | 7.36 |
| 277.1445:0.794:n | MEHP | 2.42E-04 | 0.43 | 0.50 |
| 147.0764:0.930:p | Glutamine | 4.67E-04 | 0.41 | 2.22 |
| 168.0770:0.733:p | Unknown | 2.10E-03 | 0.36 | 0.58 |
| 134.0448:0.973:p | Aspartic Acid | 7.70E-03 | 0.32 | 1.68 |
| 188.0929:0.860:n | Unknown | 9.42E-03 | 0.31 | 0.53 |
| 199.0725:0.868:n | Unknown | 1.32E-02 | 0.30 | 2.04 |
| 187.0422:1.148:n | Lactic Acid | 1.38E-02 | 0.29 | 0.82 |
| 151.0402:0.755:n | Methylparaben | 1.45E-02 | 0.29 | 0.62 |
| 213.0990:0.635:p | Unknown | 1.63E-02 | 0.29 | 2.04 |
| 163.0719:0.827:p | Unknown | 2.54E-02 | 0.27 | 1.80 |
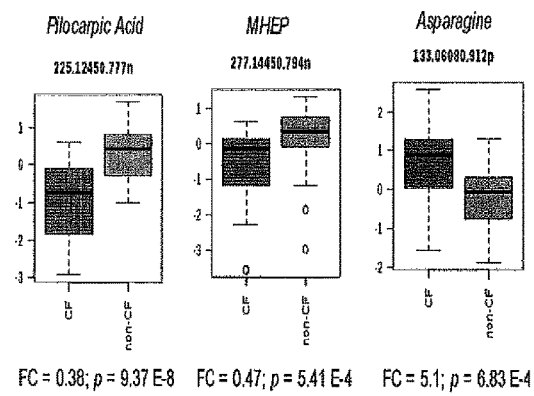
(b)
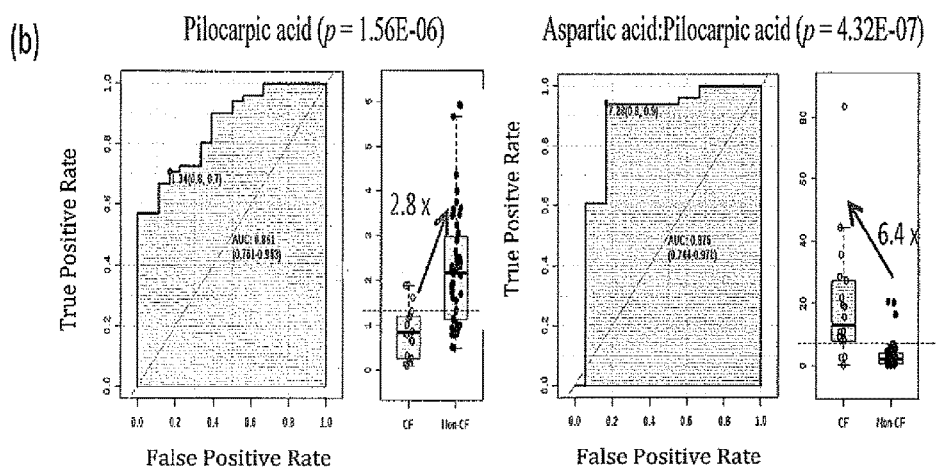
(c)
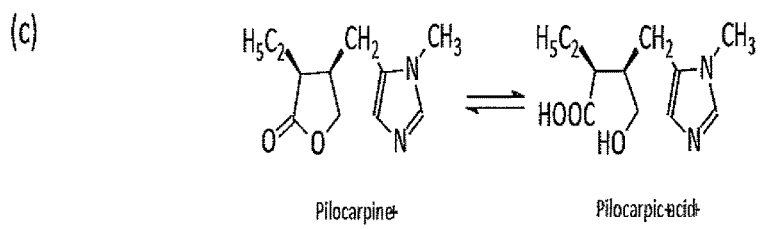

(b)

METABOLITE PANEL FOR IMPROVED SCREENING AND DIAGNOSTIC TESTING OF CYSTIC FIBROSIS

FIELD OF INVENTION

The present invention generally relates to a method for population-based screening and diagnostic testing of cystic fibrosis, and more particularly relates to a diagnostic method utilizing metabolites for the screening and/or diagnosis of cystic fibrosis.

BACKGROUND OF THE INVENTION

Cystic fibrosis (CF) is one of the most frequent recessive genetic diseases in the western world caused by mutations to the gene encoding the cystic fibrosis transmembrane conductance regulator (CFTR). More than 2,000 different mutations of the CFTR gene have been identified to date, however only a few dozen variants are of known clinical significance with ΔF508 occurring in about 70% of CF patients in North America. Mutations in the CFTR gene can lead to protein deficiency and/or loss in chloride transport function causing the formation of thick mucous at tissue surfaces. There is great clinical heterogeneity in the expression of CF that can include progressive respiratory failure, recurrent lung infections, pancreatic insufficiency, and failure to thrive, that reduces overall life expectancy. Recent evidence supports the benefits of universal CF screening of neonates (before 2 months of age), since early nutritional supplementation contributes to fewer hospitalizations, lower rates of complications with improved physical and cognitive development in children. CF patients diagnosed by newborn screening are associated with better lung function, improved nutritional status and longer survival relative to non-screened subjects. For these reasons, CF is now included within a panel of genetic diseases in newborn screening programs for pre-symptomatic diagnosis of infants at an earlier onset that results in positive clinical outcomes and lower healthcare expenditures.

A "two-tiered" approach is currently used for population-based CF screening using an algorithm based on elevated immunoreactive trypsinogen (IRT) followed by a DNA mutation panel (Parad et al. *J. Pediatrics* 2005, 147: 878), however the exact IRT threshold and total number of CFTR mutations used varies by jurisdiction (Massie et al. *Med. J Australia* 2012, 196: 67). Limitations of this primary screening strategy include a high rate of false positives (≈85-90%) as confirmed by low chloride sweat test results (<30 mM), the identification of carriers with CFTR allele variants who do not express the disease, and potential false-negatives for individuals with rare CFTR mutations within diverse populations (Castellani et al. *Curr. Opin. Pulmon. Med.* 2010, 16: 584). Furthermore, ethical concerns are related to asymptomatic carrier identification that increases costs due to referrals for diagnostic testing, genetic counseling and follow-up patient monitoring. As a result, the pilocarpine-stimulated iontophoresis sweat test remains the "gold standard" for confirmatory diagnosis of CF based on functional assessment of residual CFTR activity in terms of chloride absorptivity from skin. Since IRT and/or mutation screens provide only probable or inconclusive information regarding disease status, only 10-15% of screen-positive CF infants have elevated sweat chloride (>60 mM) with the majority of patients having low/normal chloride (<29 mM) or borderline chloride (30-59 mM). The latter outcome corresponds to an ambiguous diagnostic test result with mild/late-onset phenotypes and poorly understood natural clinical histories requiring repeat sweat testing and on-going clinical assessment.

Thus, there is a need for an improved method for the screening and diagnosis of cystic fibrosis in affected individuals which overcomes at least one of the disadvantages of prior methods.

SUMMARY OF THE INVENTION

A novel method for screening and diagnosing cystic fibrosis has now been developed which is based on one or more CF-specific metabolites measured in biological specimens.

Thus, in one aspect of the invention, a method of diagnosing cystic fibrosis or a related disorder in a human subject and treating the subject is provided comprising:
  i) determining in a biological sample from the subject the level of one or more metabolic biomarkers selected from the group consisting of L-glutamine (Gln), L-threonine (Thr), nicotinamide, O-acetyl-L-carnitine (C2), L-tyrosine (Tyr), L-histidine (His), oxidized glutathione disulphide (GSSG), 3-methyl-L-histidine (Me-His), L-serine (Ser), L-ornithine (Orn), L-proline (Pro), 3-hydroxy-L-proline (OHPro), γ-butyrobetaine (deoxy-L-carnitine), betaine glycine, glycine (Gly), L-arginine, 2-aminobutyric acid (BAIBA), creatine, L-alanine (Ala), L-proline betaine, L-kynurenine (Kyn), L-tryptophan (Trp), β-alanine (β-Ala), L-valine (Val), asymmetric dimethyl-L-arginine (ADMA), choline, guanosine, hypoxanthine (HyX), L-asparagine (Asn), L-aspartic acid (Asp), pilocarpic acid, monoethylhexylphthalic acid (MEHP), lactic acid and metabolites of biological significance exhibiting a mass-to-charge ratio (m/z) and relative migration time (RMT) when using capillary electrophoresis-mass spectrometry (CE-MS) selected from the group of a metabolite having a m/z of 310.114 [MH+] and RMT of 1.43, a metabolite having a m/z of 309.129 [MH+] and RMT of 1.283, a metabolite having a m/z of 388.109 [M+2H2+] and RMT of 1.300, a metabolite having a m/z of 294.156 [MH+] and RMT of 1.225, a metabolite having a m/z of 238.095 [MH+] and a RMT of 1.175; a metabolite having a m/z of 290.135 [MH+] and RMT of 1.225, a metabolite having a m/z of 186.088 [MH+] and RMT of 0.989, a metabolite having a m/z of 445.139 [MH+] and RMT of 0.975, a metabolite having a m/z of 168.077 [MH+] and RMT of 0.733, a metabolite having a m/z of 188.093 [M−H−] and RMT of 0.860, a metabolite having a m/z of 199.0725 [M−H−] and RMT of 0.868, a metabolite having a m/z of 213.099 [MH+] and RMT of 0.635, a metabolite having a m/z of 163.0719 [MH+] and RMT of 0.827, m/z of 92.027 [M−H−] and RMT of 0.75; a metabolite having a m/z of 252.109 [MH+] and RMT of 1.15, a metabolite having a m/z of 180.087 [MH+] and RMT of 0.73, a metabolite having a m/z of 176.07 [MH+] and RMT of 0.69;
  ii) comparing the level of the biomarker to a control level and determining the difference between the biomarker level and the control level;
  iii) determining that the subject has cystic fibrosis when the difference in the level of the biomarker in the sample is statistically different from the control level; and iv) treating the subject with one or more of an antibiotic, an anti-inflammatory, a mucus-thinning drug, a bronchodilator and a pancreatic enzyme.

In another aspect of the present invention, a method of confirming a screen-positive infant is truly affected with cystic fibrosis. The method comprises the steps of: i) determining in a biological sample from the subject the level of one or more metabolic biomarkers selected from the group consisting of L-glutamine (Gln), glycine (Gly), L-tyrosine (Tyr), L-serine (Ser), L-threonine (Thr), L-ornithine (Orn), L-proline (Pro), L-histidine (His), proline betaine, choline, creatine, hypoxanthine (HyX), guanosine (G), beta-aminobutyric acid (BAIBA), pilocarpic acid, L-asparagine (Asn), monoethylhexylphthalic acid (MEHP), L-aspartic acid (Asp), lactic acid and metabolites of biological significance exhibiting a mass-to-charge ratio (m/z) and relative migration time (RMT) when using capillary electrophoresis-mass spectrometry (CE-MS) selected from the group of a metabolite having a m/z:RMT of 186.088:0.989, 290.134:0.225, 168.077:0.733, 188.093:0.860, 199.072:0.868, and 92,0269: 0.754 ii) comparing the level of the biomarker to a control level and determining the difference between the biomarker level and the control level; and iii) confirming that the subject has cystic fibrosis when the difference in the level of the biomarker in the sample is statistically different from the control level, followed by administration of an appropriate treatment.

In a further aspect, a method of monitoring disease progression and/or response to treatment in a human subject with cystic fibrosis is provided. The method comprises:
i) determining in a biological sample from the subject the level of one or more metabolic biomarkers selected from the group consisting of L-glutamine (Gln), L-threonine (Thr), nicotinamide, O-acetyl-L-carnitine (C2), L-tyrosine (Tyr), L-histidine (His), oxidized glutathione disulphide (GSSG), 3-methyl-L-histidine (Me-His), L-serine (Ser), L-ornithine (Orn), L-proline (Pro), 3-hydroxy-L-proline (OHPro), γ-butyrobetaine (deoxy-L-carnitine), betaine glycine, glycine (Gly), L-arginine, 2-aminobutyric acid (BAIBA), creatine, L-alanine (Ala), L-proline betaine, L-kynurenine (Kyn), L-tryptophan (Trp), β-alanine (β-Ala), L-valine (Val), asymmetric dimethyl-L-arginine (ADMA), choline, guanosine, hypoxanthine (HyX), L-asparagine (Asn), L-aspartic acid (Asp), pilocarpic acid, monoethylhexylphthalic acid (MEHP), lactic acid and unknown metabolites of biological significance exhibiting a mass-to-charge ratio (m/z) and relative migration time (RMT) when using capillary electrophoresis-mass spectrometry (CE-MS) selected from the group of a metabolite having a m/z of 310.114 [MH+] and RMT of 1.43, a metabolite having a m/z of 309.129 [MH+] and RMT of 1.283, a metabolite having a m/z of 388.109 [M+2H2+] and RMT of 1.300, a metabolite having a m/z of 294.156 [MH+] and RMT of 1.225, a metabolite having a m/z of 238.095 [MH+] and a RMT of 1.175; a metabolite having a m/z of 290.135 [MH+] and RMT of 1.225, a metabolite having a m/z of 186.088 [MH+] and RMT of 0.989, a metabolite having a m/z of 445.139 [MH+] and RMT of 0.975, a metabolite having a m/z of 168.077 [MH+] and RMT of 0.733, a metabolite having a m/z of 188.093 [M−H−] and RMT of 0.860, a metabolite having a m/z of 199.0725 [M−H−] and RMT of 0.868, a metabolite having a m/z of 213.099 [MH+] and RMT of 0.635, a metabolite having a m/z of 163.0719 [MH+] and RMT of 0.827, m/z of 92.027 [M−H−] and RMT of 0.75; a metabolite having a m/z of 252.109 [MH+] and RMT of 1.15, a metabolite having a m/z of 180.087 [MH+] and RMT of 0.73, a metabolite having a m/z of 176.07 [MH+] and RMT of 0.69;
ii) comparing the level of the biomarker to a control level and determining the first difference between the biomarker level and the control level;
iii) determining the level of the biomarker at a second subsequent instance and determining the second difference between the biomarker level at the first instance and at the second instance;
iv) comparing the first and second differences and determining that the disease is progressing if the second difference is greater than the first difference, or determining that the subject is responding to treatment if the second difference is less than the first difference.

These and other aspects of the invention will become apparent from the detailed description that follows and by referenced to the following figures.

BRIEF DESCRIPTION OF THE FIGURES

FIG. 1. Overview of the population-based screening of CF based on a two-tiered IRT and DNA mutation panel followed by confirmatory sweat chloride test used previously in most jurisdictions in North America;

FIG. 4 outlines an accelerated workflow in metabolomics for biomarker discovery that takes advantage of multiplexed separations by MSI-CE-MS with higher sample throughput and data fidelity;

FIG. 8 depicts a strategy for structural elucidation of metabolites differentially expressed in dried blood spot extracts from CF subjects using accurate mass, spiking with authentic standards and collisional-induced dissociation for fragmentation of precursor ion for MS/MS spectra acquisition at different collisional energies, such as a metabolite with a m/z of 238.095 [MH$^+$] and a RMT of 1.108;

FIG. 15 depicts a machine learning algorithm based on random forests (RF) for classification of screen-positive/affected CF (category A) from screen-positive/unaffected CF infants (category B and C) based on 70 polar metabolites measured in retrospective dried blood spot (DBS) specimens by MSI-CE-MS, where (a) summarizes the predictive accuracy of the model for filtering unaffected CF infants (i.e., carriers/false-positives) with a low class error of 4.2% based on a panel of significant metabolites ranked by their mean decrease in accuracy, (b) illustrates results for pilocarpic acid and aspartic acid:pilocarpic acid via a 1-Way ANOVA/Fischer's LSD test, and (c) illustrates the conversion of pilocarpine to pilocarpic acid;

DETAILED DESCRIPTION OF THE INVENTION

Figure 2:
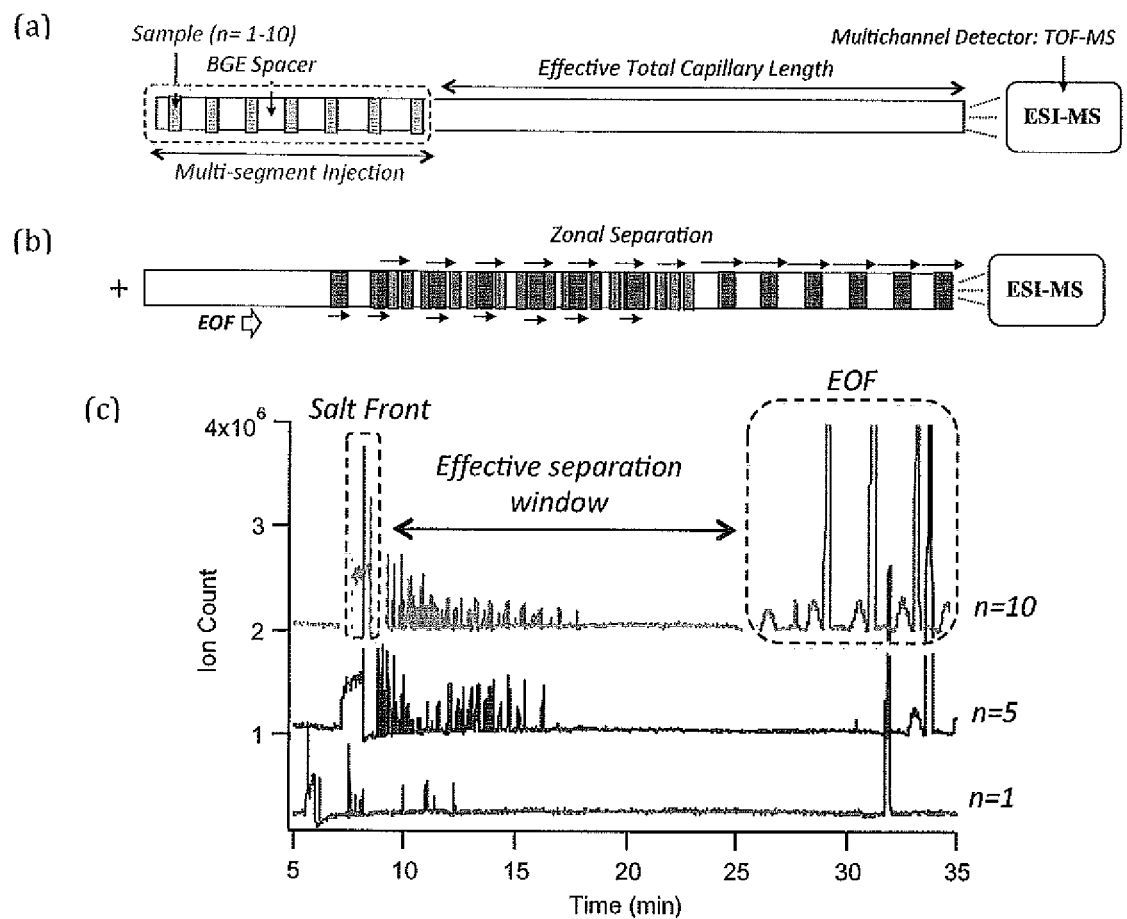
FIG. 2 depicts multi-segment injection-capillary electrophoresis (MSI-CE-MS) that is used as a multiplexed separation platform for untargeted metabolite profiling of complex biological samples that increases sample throughput by over one order of magnitude.

A novel method of diagnosing cystic fibrosis in a human subject is provided comprising: i) determining in a biological sample from the subject the level of one or more metabolic biomarkers selected from the group consisting of L-glutamine (Gln), L-threonine (Thr), nicotinamide, O-acetyl-L-carnitine (C2), L-tyrosine (Tyr), L-histidine (His), oxidized glutathione disulphide (GSSG), 3-methyl-L-histidine (MeHis), L-serine (Ser), L-ornithine (Orn), L-proline (Pro), 3-hydroxy-L-proline (OHPro), γ-butyrobetaine (deoxy-L-carnitine), betaine glycine, glycine (Gly), L-arginine, 2-aminobutyric acid (BAIBA), creatine, L-alanine (Ala), L-proline betaine, L-kynurenine (Kyn), L-tryptophan (Trp), β-alanine (β-Ala), L-valine (Val), asymmetric dimethyl-L-arginine (ADMA), choline, guanosine, hypoxanthine (HyX), L-asparagine (Asn), L-aspartic acid (Asp), pilocarpic acid, monoethylhexylphthalic acid (MEHP), lactic acid and unknown metabolites of biological significance exhibiting a mass-to-charge ratio (m/z) and relative migration time (RMT) when using capillary electrophoresis-mass spectrometry (CE-MS) selected from the group of a metabolite having a m/z of 310.114 [MH+] and RMT of 1.43, a metabolite having a m/z of 309.129 [MH+] and RMT of 1.283, a metabolite having a m/z of 388.109 [M+2H2+] and RMT of 1.300, a metabolite having a m/z of 294.156 [MH+] and RMT of 1.225, a metabolite having a m/z of 238.095 [MH+] and a RMT of 1.175; a metabolite having a m/z of 290.135 [MH+] and RMT of 1.225, a metabolite having a m/z of 186.088 [MH+] and RMT of 0.989, a metabolite having a m/z of 445.139 [MH+] and RMT of 0.975, a metabolite having a m/z of 168.077 [MH+] and RMT of 0.733, a metabolite having a m/z of 188.093 [M−H−] and RMT of 0.860, a metabolite having a m/z of 199.0725 [M−H−] and RMT of 0.868, a metabolite having a m/z of 213.099 [MH+] and RMT of 0.635, a metabolite having a m/z of 163.0719 [MH+] and RMT of 0.827, m/z of 92.027 [M−H−] and RMT of 0.75; a metabolite having a m/z of 252.109 [MH+] and RMT of 1.15, a metabolite having a m/z of 180.087 [MH+] and RMT of 0.73, a metabolite having a m/z of 176.07 [MH+] and RMT of 0.69; ii) comparing the level of the biomarker to a control level and determining the difference between the biomarker level and the control level; iii) determining that the subject has cystic fibrosis when the difference in the level of the biomarker in the sample is statistically different from the control level; and iv) treating the subject with one or more of an antibiotic, an anti-inflammatory, a mucus-thinning drug, a bronchodilator and a pancreatic enzyme.

The term "cystic fibrosis" is used herein to refer to an inherited autosomal disease associated with mutations to the gene encoding the cystic fibrosis transmembrane conductor regulator (CFTR). Commonly, CF is associated with homozygotes or compound heterozygotes having a delF508 mutation leading to CF symptoms such as pancreatic insufficiency, poor lung function and nutrient absorption. Cystic fibrosis represents a disease spectrum when considering compound heterozygotes, that results in related disorders referred to as CFTR-related metabolic syndrome (a CF-related metabolic syndrome or CFRMS), which may exhibit similar symptoms.

To conduct the method, a biological sample is obtained from a human subject. The term "biological sample" is meant to encompass any human sample that may contain relevant metabolites, including biological fluids such as, but not limited to, blood, plasma/serum, urine, sweat, saliva, sputum, cerebrospinal fluid, and for prenatal testing, amniotic fluid. Tissue biopsies from organs affected by CF may also be used, including, for example, lung, pancreas and tissue of the gastrointestinal tract. The sample is obtained from the subject in a manner well-established in the art.

Once a suitable biological sample is obtained, it is analyzed to determine the signal response or concentration of the selected biomarker(s) in the sample. Prior to analysis, the sample may be subject to processing such as extraction, filtration, centrifugation or other sample preparation techniques to provide a sample that is suitable for further analysis. For example, biological fluids may be filtered or centrifuged (e.g. ultracentrifugation) to remove solids from the sample to facilitate analysis. Tissue samples may be subject to extractions in order to provide an analyzable sample such as dried blood samples deposited on filter cards. As one of skill in the art will appreciate, biomarker level may be determined using one of several techniques established in the art that would be suitable for detecting such biomarkers, e.g. polar metabolites, in a biological sample, including mass spectrometry, chromatographic techniques such as high performance liquid chromatography and gas chromatography, immunoassay or enzyme-based assays with colorimetric, fluorescence or radiometric detection. As one of skill in the art will appreciate, CF-specific markers may be analyzed directly or may be chemically derivatized for analysis, and may be analyzed by comparison against stable-isotope internal standards.

In a preferred embodiment, biomarker detection using a mass spectrometry (MS)-based method is used. Suitable MS-based methods for use include direct infusion-mass spectrometry, electrospray ionization (ESI)-MS, desorption electrospray ionization (DESI)-MS, direct analysis in real-time (DART)-MS, atmospheric pressure chemical ionization (APCI)-MS, electron impact (EI) or chemical ionization (CI), as well as MS-based methods coupled with a separation technique, such as liquid chromatography (LC-MS), gas chromatography (GC-MS), or capillary electrophoresis (CE-MS) mass spectrometry.

In other embodiments, the level of a biomarker in a sample may be measured by immunoassay using an antibody specific to the target biomarker. The antibody binds to the biomarker and bound antibody is quantified by measuring a detectable marker which may be linked to the antibody or other component of the assay, or which may be generated during the assay. Detectable markers may include radioactive, fluorescent, phosphorescent and luminescent (e.g. chemiluminescent or bioluminescent) compounds, dyes, particles such as colloidal gold and enzyme labels. The term "antibody" is used herein to refer to monoclonal or polyclonal antibodies, or antigen-binding fragments thereof, e.g. an antibody fragment that retains specific binding affinity for the target biomarker. Antibodies to the target biomarkers may be commercially available. Alternatively, antibodies to the target biomarkers may also be raised using techniques conventional in the art. For example, antibodies may be made by injecting a host animal, e.g. a mouse or rabbit, with the antigen (target biomarker), and then isolating antibody from a biological sample taken from the host animal. Alternative affinity ligands that bind to CF-specific metabolites may also be utilized for measurement of CF metabolites, such as DNA or RNA-based aptamers derived from systematic evolution of ligands by exponential enrichment (SELEX).

Different types of immunoassay may be used to determine the level of target biomarkers in a sample, including indirect immunoassay in which the biomarker is non-specifically immobilized on a surface; sandwich immunoassay in which the biomarker is specifically immobilized on a surface by linkage to a capture antibody bound to the surface; and a competitive binding immunoassay in which a sample is first combined with a known quantity of biomarker antibody to bind biomarker in the sample, and then the sample is exposed to immobilized biomarker which competes with the sample to bind any unbound antibody. Enzyme Linked ImmunoSorbent Assay (ELISA) may also be used to determine the level of a biomarker in a sample. In this case, the biomarker to be analyzed is generally immobilized on a solid support, complexed with an antibody to the biomarker which is itself linked to an enzyme indicator, such as horseradish peroxidase (HRP), alkaline phosphatase (AP), β-galactosidase, acetylcholinesterase and catalase. Detection may then be accomplished by incubating this enzyme-complex with a substrate for the enzyme that yields a detectable product.

The method includes the measurement of at least one metabolite as a specific biomarker for CF from a biological sample. Preferably, the level of at least two or more biomarkers is determined to screen or diagnose cystic fibrosis, for example, the level of between two to fifteen biomarkers as part of a panel of top-ranked metabolites to enhance sensitivity and specificity, e.g. between two and ten biomarkers are determined in a sample, and more preferably, the level of between two and five biomarkers are determined in a sample, for use to screen or diagnose cystic fibrosis.

Once the level of the selected biomarker(s) is determined, the level is compared to a control level to determine the average fold-change (FC) difference and statistical significance (p-value) between the biomarker measured in cystic fibrosis group (i.e., affected patients with CF with high sweat chloride and at least one disease-causing CFTR mutation) relative to a control group (e.g., healthy/screen-negative infant or screen-positive/unaffected infant). The level of some of the metabolite biomarkers is increased in cystic fibrosis in comparison to a control level. Examples of biomarkers that exhibit increased levels in cystic fibrosis relative to unaffected subjects (i.e. fold-change >1) include L-tryptophan, L-citrulline, β-alanine, L-ornithine, O-butyryl-L-carnitine (C4), L-arginine, L-valine, L-carnitine, L-lysine, pilocarpic acid, 3-hydroxy-L-proline, and other metabolites as shown in Tables 1 and 2. Other metabolite biomarkers exhibit a reduced level in cystic fibrosis in comparison to unaffected subjects (i.e., fold-change <1), such as L-glutamine, L-arginine, oxidized glutathione disulfide, O-butyryl-L-carnitine, L-kynurenine, and other metabolites as shown in Tables 1 and 2. The term "control level", as it is used herein, is the level of a selected metabolite biomarker detected in a sample from a healthy or screen-positive yet unaffected subject (i.e. a carrier) who does not have cystic fibrosis. Preferably the control value is a mean control value obtained from a healthy population of matched subjects (e.g. age-, gender- and/or ethnically-matched to a population).

In addition to the quantitation of selected biomarkers, a ratiometric determination of two biomarkers may be calculated, i.e. the ratio of the levels of two biomarkers from a sample, for comparison against a control value, i.e. the ratio of the control levels of the two selected biomarkers. For example, the ratio of the level of the biomarker, arginine, and the level of the biomarker, citrulline, may be determined in a biological sample, and compared to a control ratio of the levels of these two biomarkers, to determine the difference between the ratio in the sample and the control ratio. Preferred ratiometric determinations for use in the present method are between a metabolite biomarker that exhibits an increased level in cystic fibrosis, e.g. oxidized glutathione, tryptophan, citrulline, ornithine, valine, lysine, asymmetric-dimethyl-L-arginine, beta-alanine, 3-hydroxy-L-proline, 5-hydroxy-L-lysine, histadine, and other metabolites that exhibit a fold-change of greater than 1 over a normal (control) level of the metabolite, and a metabolite biomarker that exhibits a reduced level in cystic fibrosis, e.g. nicotinamide, arginine, C4, 5-deoxyadensosine, aspartic acid, and other metabolites that exhibit a fold-change of less than 1 over a normal (control) level of the metabolite. Such a ratio further amplifies the fold-change of the selected biomarkers and increases statistical significance (p value) for CF screening or diagnosis, while also correcting for differences in sample volume in a specimen analyzed (e.g. dried blood spot).

A human subject is determined to have cystic fibrosis when the difference in the level of one or more biomarkers in a biological sample is statistically different from the control levels of these biomarkers, and/or when the difference in a ratiometric determination between two biomarkers is statistically different from the control ratio between these biomarkers above a minimum control threshold established for a population. The determination of statistical significance is well-established in the art. Statistical significance is attained when a p-value is less than the significance level. The p-value is the probability of observing an effect given that the null hypothesis is true whereas the significance or alpha ($\alpha$) level is the probability of rejecting the null hypothesis given that it is true. Generally, a statistically significant difference, i.e. increase or decrease, in the level of a biomarker in accordance with the present method, is a difference in the level of the biomarker from the control level of at least about 5%, or greater, e.g. at least about 10%, 15%, 20%, 25% or more. When performing multivariate statistical analysis during biomarker discovery in metabolomics, corrected p-values are often used to correct for multiple hypothesis testing in order to reduce false discoveries, such as the use of a false discovery rate (q<0.05) or a more conservative Bonferroni correction.

In one embodiment, the biological sample is a dried blood spot sample, and the biomarker(s) is selected from the group consisting of L-tryptophan, L-citrulline, L-glutamine, oxidized glutathione disulfide, β-alanine, L-proline, L-ornithine, O-butyryl-L-carnitine, L-arginine, L-valine, L-carnitine, L-kynurenine, L-lysine, L-isoleucine, L-asparagine, L-aspartic acid, L-histidine, L-serine, L-tyrosine, and L-threonine, 3-methyl-L-histidine, 3-hydroxy-L-proline, glycine, trimethylamine N-oxide, asymmetric N-dimethyl-L-arginine, 5-hydroxy-L-lysine, adenine, guanine, guanosine, hypoxanthine, 2-deoxyadenosine, O-acetyl-L-carnitine, 2-aminobutyric acid, betaine glycine, γ-butyrobetaine (deoxy-L-carnitine), 3-methyl-L-histidine, (deoxy-L-carnitine), creatine, nicotinamide, and metabolites exhibiting a mass-to-charge ratio (m/z) and relative migration time (RMT) when using capillary electrophoresis-mass spectrometry (CE-MS) selected from the group of a metabolite having a m/z of 445.139 and RMT of 1.325; a metabolite having a m/z of 388.109 and RMT of 1.300, a metabolite having a m/z of 310.114 and RMT of 1.430, a metabolite having a m/z of 309.129 and RMT of 1.283, a metabolite having a m/z of 294.156 and RMT of 1.225, a metabolite having a m/z of 290.135 and RMT of 1.225, a metabolite having m/z of 252.109 [MH$^+$] and a RMT of 0.872; a metabolite having a m/z of 238.095 [MH$^+$] and a RMT of 1.108; a metabolite having a m/z of 180.087 [MH$^+$] and a RMT of 0.730; a metabolite having a m/z of 252.109 [MH$^+$] and a RMT of 1.274; a metabolite having a m/z of 298.053 [MH$^+$] and a RMT of 0.794; a metabolite having m/z of 252.109 [MH$^+$] and a RMT of 1.152; a metabolite having a m/z of 186.088 and RMT of 0.989, a metabolite having a m/z of 176.071 [MH$^+$] and a RMT of 0.694; and a metabolite having a m/z of 104.071 [MH$^+$] and a RMT of 0.772.

In another embodiment, the biological sample is a dried blood spot sample, and the biomarker(s) is selected from the group consisting of L-glutamine, L-proline, L-ornithine, L-arginine, glycine, oxidized glutathione disulfide (GSSG), hypoxanthine, O-acetyl-L-carnitine, 2-aminobutyric acid, betaine glycine, γ-butyrobetaine (deoxy-L-carnitine), 3-methyl-L-histidine, guanosine, creatine, L-histidine, nicotinamide, L-serine, L-tyrosine, proline betaine, choline and L-threonine, and metabolites exhibiting a mass-to-charge ratio (m/z) and relative migration time (RMT) when using capillary electrophoresis-mass spectrometry (CE-MS) selected from the group of a metabolite having a m/z:RMT and molecular formula as measured by CE-ESI-MS, of a metabolite having a m/z of 445.139 and RMT of 1.325; a metabolite having a m/z of 388.109 and RMT of 1.300, a metabolite having a m/z of 310.114 and RMT of 1.430, a metabolite having a m/z of 309.129 and RMT of 1.283, a metabolite having a m/z of 294.156 and RMT of 1.225, a metabolite having a m/z of 290.135 and RMT of 1.225, and a metabolite having a m/z of 186.088 and RMT of 0.989.

In a further embodiment, the biological sample is a sweat sample, and the biomarker(s) is selected from the group consisting of L-citrulline, pilocarpic acid, 3-hydroxy-L-proline, L-arginine, L-tyrosine, L-phenylalanine, hypoxanthine, pilocarpine, monoethylhexylphthalic acid and L-lysine, and metabolites exhibiting a mass-to-charge ratio (m/z) and relative migration time (RMT) when using capillary electrophoresis-mass spectrometry (CE-MS) selected from the group of a metabolite having a m/z of 280.078 [M−H$^-$] and a RMT of 0.967; a metabolite having a m/z of 115.040 [M−H$^-$] and a RMT of 1.076; a metabolite having a m/z of 160.062 [M−H$^-$] and a RMT of 0.917; a metabolite having a m/z of 201.077 [M−H$^-$] and a RMT of 0.849; a metabolite having a m/z of 129.056 [M−H$^-$] and a RMT of 1.019; a metabolite having a m/z of 257.114 [M−H$^-$] and a RMT of 0.835; a metabolite having a m/z of 235.118 [MH$^+$] and a RMT of 0.768; a metabolite having a m/z of 194.138 [MH$^+$] and a RMT of 0.721; a metabolite having a m/z of 370.053 [MH$^+$] and a RMT of 0.820; a metabolite having a m/z of 247.037 [MH$^+$] and a RMT of 0.565; a metabolite having a m/z of 139.050 [MH$^+$] and a RMT of 0.686; a metabolite having a m/z of 168.077 and RMT of 0.733, a metabolite having a m/z of 188.093 and RMT of 0.860, a metabolite having a m/z of 199.0725 and RMT of 0.868, a metabolite having a m/z of 213.099 and RMT of 0.635, and a metabolite having a m/z of 163.0719 and RMT of 0.827; and a metabolite having a m/z of 280.024 [MH$^+$] and a RMT of 0.687.

Certain of the metabolite biomarkers in sweat exhibit an increased level in cystic fibrosis in comparison to a control level, e.g. glutamine, L-ornithine, citrulline, 3-hydroxy-L-proline, tyrosine, phenylalanine, pilocarpine, lysine, and other metabolites that exhibit a fold-change of greater than 1 over a normal (control) level of the metabolite. Other metabolite biomarkers exhibit a reduced level in cystic fibrosis in comparison to a control level, e.g. MEHP, pilocarpic acid, arginine, hypoxanthine, and a metabolite that exhibits a fold-change of less than 1 over a normal (control) level of the metabolite.

In another aspect of the present invention, a method of distinguishing between affected individuals (i.e. a newborn with cystic fibrosis) and a screen-positive yet unaffected individual (i.e. a false positive or unaffected carrier of the recessive condition). This method is particularly useful for distinguishing truly affected infants from screen-positive infants who are not affected with the disease. The method comprises the steps of: i) determining in a biological sample from the subject the level of one or more metabolic biomarkers selected from the group consisting of L-glutamine, L-glycine, L-tyrosine, L-serine, L-threonine, L-ornithine, L-proline, L-histidine, proline betaine, choline, creatine, hypoxanthine, guanosine (G), beta-aminobutyric acid (BAIBA), an ion (186.088:0.9887 m/z:RMT) and an ion having a m/z:RMT ratio of 290.1347:0.2247; ii) comparing the level of the biomarker to a control level and determining the difference between the biomarker level and the control level; and iii) determining that the subject has cystic fibrosis when the difference in the level of the biomarker in the sample is statistically different from the control level.

Following diagnosis of cystic fibrosis, an appropriate treatment is selected. The treatment may include nutritional supplementation (such as fat-soluble vitamins) to ensure proper growth, potentiators and/or correctors (such as ivacaftor and lumacaftor) to treat the underlying protein mutation, one or more of antibiotics to treat and prevent lung infections (such as amoxicillin and methicillin); anti-inflammatory medications to lessen lung exacerbations (such as prednisone, ibuprofen); mucus-thinning drugs to improve lung function (such as N-acetylcysteine, hypertonic saline and dornase alfa); bronchodilators (such as albuterol, metaproterenol); and pancreatic enzyme supplements (such as various commercial formulations for pancreatic replacement therapy).

The present methods advantageously provide a means to screen and diagnose CF in a cost-effective manner while providing the necessary sensitivity with improved specificity as compared to conventional two-tiered screens (e.g., IRT and CFTR mutation panel). This method avoids identification of CF carriers, and thus, eliminates the ethical concerns of population-based CF screening in newborn screening programs that is limited by high rates of false positives. The present methods also enable differential diagnosis of the CF disease spectrum notably in cases associated with ambiguous or inconclusive sweat chloride test results. As a result, metabolite-based biomarkers associated with CF may be measured by mass spectrometry as a multiplexed instrumental platform already available in most clinical laboratories, eliminating the need for CF-specific immunoassays (e.g. IRT) and population-based genetic testing.

In addition to use to diagnose cystic fibrosis, the present methods may also be used to predict disease progression and/or monitor treatment response to therapy. In this regard, for a human subject determined to have cystic fibrosis, by the present or other diagnostic method, the present method may subsequently be used to determine the level of one or more of the metabolite biomarkers in a biological sample from the subject. The determination of the level of the metabolite biomarker is determined on at least two occasions. In this case, the difference in a first level of the biomarker from a control level (which may be a baseline level previously determined in the human subject) is determined (a first difference) and compared to a subsequent difference (second difference) which is the difference between a subsequent determined biomarker level and the control level. If the difference in biomarker level increases over time (difference 1 is less than difference 2), this indicates that the disease is progressing (or treatment is not effective), while no change in the difference of biomarker levels over time indicates that the disease is not progressing (or treatment may be effective), and a decrease in the difference of biomarker levels over time indicates disease remission (or treatment is effective).

Embodiments of the invention are described in the following examples which are not to be construed as limiting.

EXAMPLE 1

Determination of Metabolites Associated With Cystic Fibrosis

Chemicals and Reagents. Deionized water used for aqueous buffer and stock preparations were obtained from a Thermo Scientific Barnstead EasyPure II ultrapure water system (Cole Parmer, Vernon Hills, Ill., USA). Ammonium acetate, formic acid, acetic acid, 3-chloro-L-tyrosine (Cl-Tyr), 2-[4-(2-hydroxyethyl)piperazin-1-yl]ethanesulfonic acid (HEPES), and analyte standards were purchased from Sigma-Aldrich (St. Louis, Mo., USA). HPLC-grade methanol (Caledon, Georgetown, ON, Canada) and HPLC-grade acetonitrile (Honeywell, Muskegon, Mich., USA) were used to prepare sheath liquid and background electrolyte (BGE), respectively. Acylcarnitine standards were graciously provided by Dr. Murray Potter at McMaster University. Polar standards were prepared in water and stored at 4° C., whereas acylcarnitine standards were prepared in methanol and stored at −20° C.

Blood Spot Collection and Sample Preparation. Proficiency testing (PT) and quality assurance (QA) dried blood spot samples were acquired from the Newborn Screening Quality Assurance Program at the Centers for Disease Control and Prevention (Atlanta, Ga., USA). Duplicate punches (technical replicates) of PT and QA dried blood spot specimens that simulate phenylketonuria (PKU), maple syrup urine disease (MSUD), citrullinemia (CIT), medium chain acyl-CoA dehydrogenase deficiency (MCADD) and glutaric acidemia type-1 (GA-1) were prepared by spiking in known amounts of primary biomarkers above accepted cut-off limits (McHugh et al. *Genet. Med.* 2011, 13: 230) using reference standards to pooled blood from consenting adult donors. Duplicate punches of two cystic fibrosis (CF) samples were each made from the blood of a consenting adult with at least one CFTR mutation. A pooled, quality control (QC) sample was made at the time of analysis by combining the reconstituted filtrates of multiple, negative control dried blood spot samples derived from Newborn Screening Ontario at the Children's Hospital of Eastern Ontario (CHEO). Samples were stored at −80° C. until analyzed. Samples were 3.2 mm disks corresponding to approximately ~3.4 µL of whole blood. Disks were placed in 0.5 mL centrifuge tubes containing 100 µL of methanol. Analytes were extracted from the disk via sonication for 10 min and then the methanolic extract was filtered using a Nanosep 3K Omega 3 kDa MWCO ultracentrifugation tube (Pall Life Sciences, MI, USA) at 14,500 rpm for 10 min. The resulting filtrate was dried down in a Vacufuge vacuum concentration at room temperature (Eppendorf, New York, USA) and reconstituted in 30 µL of sample solution (200 mM ammonium acetate, 25% acetonitrile, 25 µM Cl-Tyr, 25 µM HEPES, pH 5.0) prior to analysis.

Sweat Specimen Collection and Sample Preparation. Stimulated human sweat samples were collected from screen-positive infants at the Cystic Fibrosis Clinic at McMaster University. Sweating was induced by pilocarpine iontophoresis using a Webster Model 3700 Macroduct® Sweat Capillary Collection System (Wescor Inc. Logan, Utah, USA) with electrodes composed of solid agar discs containing 0.5% w pilocarpine nitrate which were attached to the subject's right forearm for 5 min at 1.5 mA. Sweat samples (>30 µL) were collected via a spiral capillary tube containing blue dye for visual confirmation prior to storage at −20° C. Chloride measurements for sweat were performed by a chloridometer via coulometric titration with silver ions using a temperature-controlled conductivity cell (Wescor Sweat-Check Model 3120). All sweat samples were diluted in de-ionized water with internal standards prior to analysis.

Instrumentation and Conditions. All CE-MS experiments were performed on an Agilent G7100A CE system (Agilent Technologies Inc., Mississauga, ON, Canada) with a coaxial sheath liquid dual Agilent Jetstream electrospray ion source interface to an Agilent 6230 TOF-MS. Acquisition was performed using Agilent MassHunter Workstation LC/MS Data Acquisition Software version B.05.01 and all data processing was performed using MassHunter Qualitative Analysis Software version B.06.00. All separations were performed using uncoated fused-silica capillaries (Polymicro Technologies, AZ, USA) with 50 uM ID and 120 cm length with an applied voltage of 30 kV at 25° C. The BGE was 1 M formic acid, with 15% v acetonitrile (pH 1.8). Two CE-MS configurations were used in this work depending on the requirement for high sample throughput or improved concentration sensitivity. The main configuration used for targeted metabolite profiling of known biomarkers and untargeted metabolomic studies of CF and normal dried blood spot extracts was based on multi-segment injection (MSI)-CE-MS (Kuehnbaum et al. *Anal. Chem.* 2013, 85: 10664), whereas a series of hydrodynamic injections alternating between a sample (5 s at 100 mbar) and BGE/spacer (40 s at 100 mbar) was performed for a total of either seven or five sample segments analyzed simultaneously within a single run. In cases when increased concentration sensitivity was needed for detection of low abundance metabolites of clinical relevance, on-line sample pre-concentration with CE-MS (Lee et al. *Anal. Chem.* 2007 79: 403) was performed using a single extended hydrodynamic injection of sample (90 s at 100 mbar) followed by BGE (60 s at 100 mbar) prior to voltage application. Between runs, the capillary was flushed with BGE for 15 min (at 950 mbar) to avoid sample carry-over. The sheath liquid was 60:40 MeOH:$H_2O$ with 0.1% formic acid supplied at a flow rate of 10 uL/min by an Agilent 1260 Infinity isocratic pump. Purine and hexakis(2,2,3,3-tetraflurorpropoxy)phosphazine (HP-921) were spiked into the sheath liquid at 0.02% v as reference ions at m/z 121.050873 and m/z 922.009798 for real-time internal mass calibration. The TOF-MS was operated in positive ion mode with a mass range of m/z 50-1700 with an acquisition rate of 2 Hz and an acquisition time of 500 ms. The dual AJS ESI settings were as follows: dry gas=8 L/min at 300° C., nebulizer=10 psi, sheath gas=3.5 L/min at 195° C., VCap=2000 V, Nozzle voltage=2000 V, whereas the TOF-MS voltage settings were Fragmentor=120 V, skimmer=65 V and Oct 1 RF=750 V.

Sample Injection Configuration and Data Workflow. Preliminary studies involving confirmatory analysis of known primary biomarkers of several IEMs made use of a seven-segment injection format in MSI-CE-MS to maximize sample throughput. In this case, duplicate injections of three diseases (analyst-blinded) was analyzed within a single run along with a pooled healthy/normal sample that served as a reference/negative control as well as internal QC when evaluating between-run variances. Asymmetric signal patterning was used to encode information temporally within a separation based on the specific dilution pattern used among pairs of samples. In this way, the origin of aberrant metabolite levels is readily identified based on the unique signal pattern detected for ions derived from a duplicate set of sample injections. This was useful particularly in cases in which ions were undetected in certain samples/diseases within the seven segment injection series. The dilution pattern used for pairs of samples comprised a signal pattern corresponding to 1:2, 1:1, 2:1 (as six sample segments) together with the QC (as seventh segment). The six IEMs were randomly split into two groups of three and one punch from each IEM was extracted and analyzed as previously described. The second punch was extracted and analyzed separately as a technical replicate for a total of four measurements (n=4). Follow-up studies on differentially expressed metabolites in CF were performed using a five-segment injection format in MSI-CE-MS to maximize resolution of any isomeric or isobaric compounds. In this case, the asymmetric signal pattern used for analysis involved a two-way comparison of CF relative to healthy/normal dried blood spot extracts, which corresponded to 1:2 (CF), buffer blank, 1:1 (normal/healthy). The injection order was then reversed to negate any positional impacts on sample ionization. The same procedure was repeated for a second CF punch, for a total of eight runs (n=8) when using MSI-CE-MS. Instrumental duplicate analyses were performed for each CF punch using on-line sample pre-concentration with CE-MS along with an instrumental duplicate analysis of the QC when analyzing low abundance metabolites that were not detected by MSI-CE-MS.

Calibration and Method Validation. Calibration curves for metabolite standards were performed and analyzed in triplicate (n=9) by serial dilution in 200 mM ammonium acetate, 25% acetonitrile, pH 5.0 with 25 µMCl-tyr as the internal standard. Linearity was measured over a 400-fold range for polar metabolites and over a 200-fold range for medium and long-chain acylcarnitines. Spike-recovery studies into a pooled QC sample were performed for primary markers of IEMs at three concentration levels, namely 50% of normal concentration, 75% of elevated disease concentration and the midpoint. Concentrations of spikes were adjusted slightly to ensure a significant response change relative to baseline levels detected in pooled dried blood spots from healthy infants. Percent recovery was calculated as [(measured concentration−endogenous concentration)/added concentration×100]. Repeatability of the method was determined by analysis of three technical replicates of pooled dried blood spot extracts using a seven sample segment injection format in MSI-CE-MS (n=21).

Statistical Analysis. All electropherograms were generated using Igor Pro 5.0 software (Wavemetric Inc., Lake Oswego, Oreg.). A dilution trend filter was used to rigorously filter out chemical and biochemical noise while characterizing authentic metabolites derived from dried blood spot extracts from healthy/normal infants (Kuehnbaum et al. *Anal. Chem.* 2013, 85: 10664). Cationic metabolites were included in the final data matrix if their relative response ratio had acceptable precision (CV<30%) and good linearity upon serial dilution ($R^2$>0.90) without a blank signal corresponding to a buffer filtrate sample. Complementary multivariate statistical analysis methods were used for classification of CF-specific biomarkers relative to normal/healthy controls comprising 80 cationic metabolites analyzed from two technical replicates of dried blood spot extracts analyzed as four replicate injections (n=2×4=8) when using MSI-CE-MS. Unsupervised data exploration was performed using volcano plots (fold-change>2.0; Bonferroni-corrected p<1 E-4) and supervised data analysis using partial least squares-discriminant analysis (PLS-DA) with log-transformed and autoscaled data using Metaboanalyst 2.0 (Xia et al. *Nucleic Acids Res.* 2012, 40: W127), whereas receiver operating characteristic (ROC) curves were used for classification of single (untransformed data) or ratiometric (log-transformed data) biomarkers using ROCCET (Xia et al. *Metabolomics* 2013, 9: 280).

Results

FIG. 2 shows the injection sequence configuration used in MSI-CE-MS that involves a series of short injection segments of "seven identical" samples containing a standard mixture of polar metabolites that are each displaced by a spacer comprised of the buffer (Kuehnbaum et al. *Anal. Chem.* 2013, 85: 10664). In this case, up to a third of the total capillary length is filled with multiple segments of samples and spacers in order to allow for sufficient resolution, desalting and peak capacity in the separation. To maximize sample throughput, short sample injection plugs are used with an optimum spacer length to allow for sufficient displacement of each sample segment that is needed for resolution of isomeric/isobaric ions prior to ionization. If greater sensitivity is desired, fewer sample plugs can be introduced but with a longer segment length (i.e., sample volume) injected to allow for on-line pre-concentration by CE (R. Lee et al. *Anal. Chem.* 2007 79: 403). High throughput metabolite profiling is achieved by MSI-CE-MS since seven sample plugs (i.e., dried blood spot extracts) are analyzed simultaneously within a single run with no loss in separation performance, such as resolution of three isomers of L-leucine (Leu, Ile, allo-Ile), whereas the high mass resolution of the time of flight (TOF)-MS permits resolution of co-migrating ions, such as L-phenylalanine (Phe) and L-citrulline (Cit).

Figure 3:
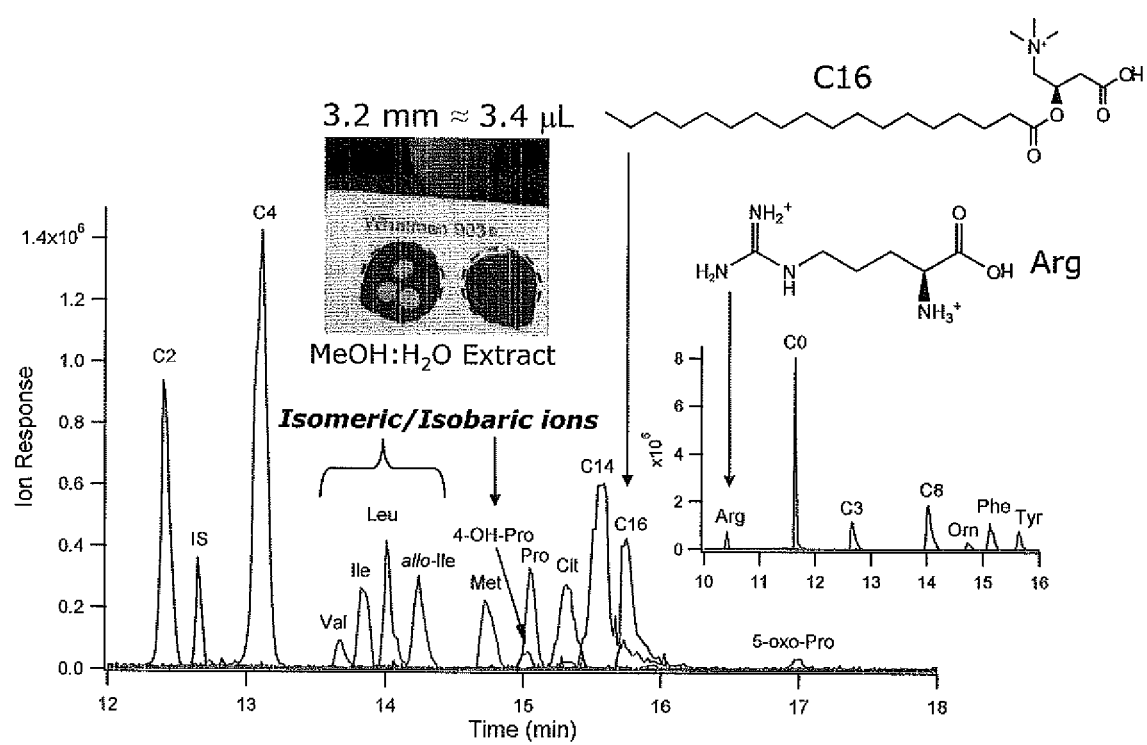
FIG. 3 depicts a wide array of polar metabolites from dried blood spot extracts that can be analyzed by MSI-CE-MS with high selectivity, including various amino acids and acylcarnitines used as primary or secondary markers of specific in-born errors of metabolism.

FIG. 3 highlights the resolution of a wide variety of polar metabolites by CE-MS derived from methanol-based extracts of dried blood spots, including various amino acids and acylcarnitines that are used as primary, secondary or ratiometric markers of specific in-born errors of metabolism (IEM). CE provides a high efficiency separation platform for resolution of isobaric/isomeric ions in complex and highly saline biological samples prior to electrospray ionization-mass spectrometry as required for improving selectivity and quantitative performance.

FIG. 4 outlines an accelerated workflow in metabolomics for biomarker discovery that takes advantage of multiplexed separations by MSI-CE-MS, such as a seven-segment format which captures dynamic metabolomic responses to strenuous exercise for individual subjects, as well as their adaptive responses to exercise training (Kuehnbaum et al. *Electrophoresis* 2015, doi: 10.1002/elps.201400604). For instance, hypoxanthine was identified as a plasma marker of energetic stress associated with untrained subjects that is related to the purine degradation cycle due to irreversible ATP hydrolysis with active muscle contraction. A similar approach for biomarker discovery was performed to identify metabolites as markers associated with cystic fibrosis (CF) in affected subjects (e.g. infant and adults) by untargeted metabolite profiling of dried blood spot extracts and pilocarpine-stimulated sweat specimens using MSI-CE-MS in conjunction with multivariate statistical methods.

Figure 5:
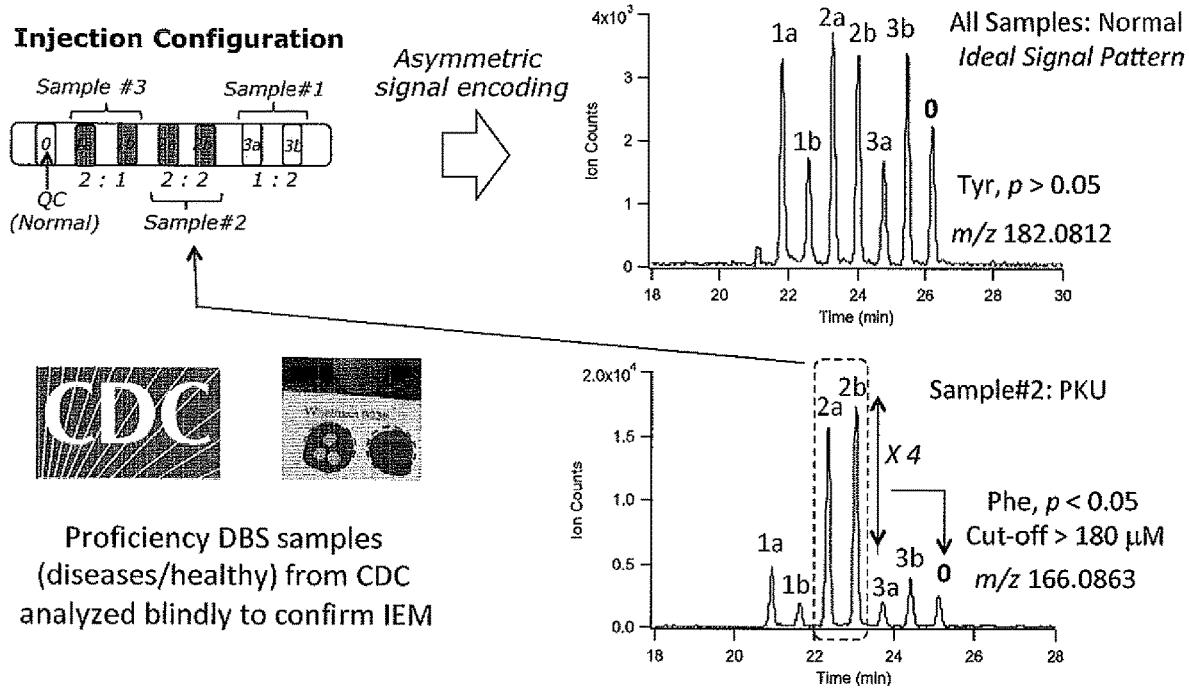
FIG. 5 depicts an asymmetric signal pattern recognition approach used in MSI-CE-MS for unambiguous identification of putative markers associated with in-born errors of metabolism (IEM) relative to a pooled healthy sample as quality control (QC), such as elevation in L-phenylalanine that is associated with phenylketonuria (PKU)

FIG. 5 depicts an asymmetric signal pattern recognition approach used in MSI-CE-MS for unambiguous identification of pmarkers associated with in-born errors of metabolism (IEM) relative to a pooled healthy sample as quality control (QC), such as elevation in L-phenylalanine that is associated with phenylketonuria (PKU). In this case, three paired samples were analyzed in series, but were diluted in such a way as to generate a distinct signal pattern to facilitate biomarker discovery with high fidelity. For instance, there is no evidence of tyrosinemia since ion signals for L-tyrosine are not significantly different between pairs of samples (i.e., disease controls), as well as QC (i.e., healthy reference sample). In contrast, a significant elevation (fold-change >4 relative to healthy/normal; p<1 E-4) of L-phenylalanine above acceptable cut-off limits is indicative of PKU that is associated with the middle pair of samples appearing as a "doublet". In all cases, the same ion is directly compared with other diseases and a pooled normal/healthy sample (QC) within a single run. Thus, MSI-CE-MS serves as a multiplexed separation platform for confirmatory testing of screen-positive samples identified by MS/MS due to its high selectivity, excellent precision and good quantitative performance while using a single non-isotope labeled internal standard. This approach was applied to several other IEM (e.g., citrullinemia, maple syrup urine disease etc.) by measuring known markers in dried blood spot extracts prior to performing metabolomic studies for biomarker discovery in CF.

Figure 6:
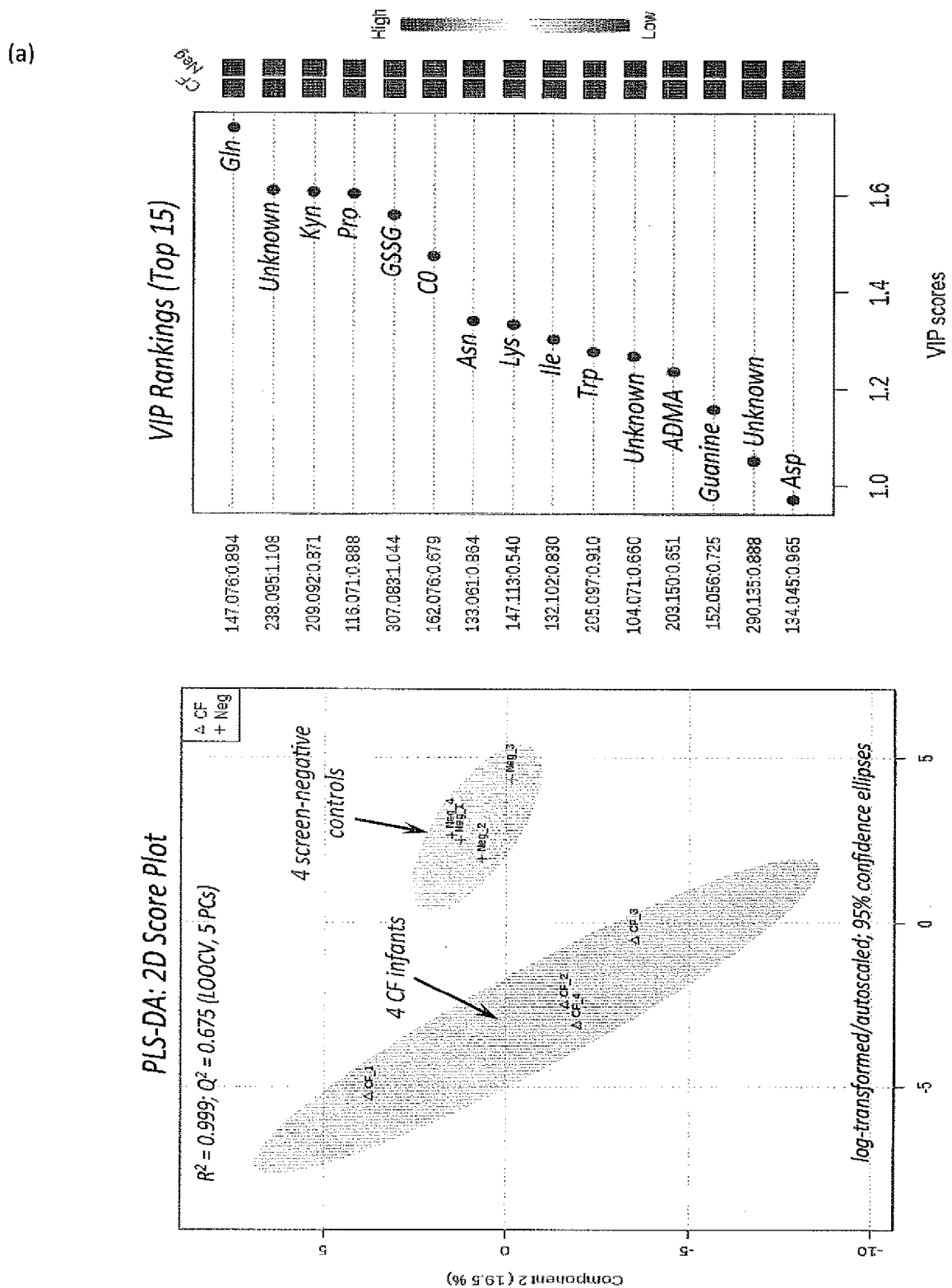
FIG. 6 depicts multivariate statistical analysis of 36 authentic metabolites measured in dried blood spot (DBS) extracts by MSI-CE-MS for the discovery of putative markers differentially expressed in affected CF infants (n=4) relative to healthy/screen-negative controls (n=4) when using (a) a 2D scores plot in partial-least squares discriminate analysis (PLS-DA) with markers annotated by their variable importance in projection (VIP) ranking and (b) receiver operating characteristic (ROC) curves for single or ratiometric CF-specific markers.

FIG. 6 depicts multivariate statistical analysis of 36 authentic metabolites measured in dried blood spot (DBS) extracts by MSI-CE-MS for the discovery of markers differentially expressed in affected CF infants (n=4) relative to healthy/screen-negative controls (n=4) when using (a) a 2D scores plot in partial-least squares discriminate analysis (PLS-DA) with markers annotated by their variable importance in projection (VIP) ranking and (b) receiver operating characteristic (ROC) curves for single or ratiometric CF-specific markers. Excellent discrimination of infants confirmed with CF (i.e., sweat chloride >60 mM) from screen-negative healthy controls is feasible when analyzing a panel of polar metabolites derived from methanol-based dried blood spot extracts with good accuracy ($R^2=0.999$) and robustness ($Q^2=0.675$) when using leave-one-out-at-a-time cross-validation. The VIP ranking summarizes the most significant metabolites associated with CF based on their measured normalized responses after log-transformation and autoscaling, such as L-glutamine and L-kynurenine (both lower in CF), as well as L-carnitine and a metabolite with a m/z of 238.095 and a RMT of 1.108 (both higher in CF). Alternatively, ROC curves can be used to select and rank CF-specific markers based on their ability to classify infants with CF with high sensitivity and specificity (in both cases area under the curve, AUG >1.00) based on an optimum threshold cut-off value including single and ratiometric markers, such as L-glutamine and L-glutamine:L-carnitine ratio, respectively. Metabolites that have a high AUC value, a high average fold-change and/or a low p-value are considered markers for CF screening.

Figure 7:
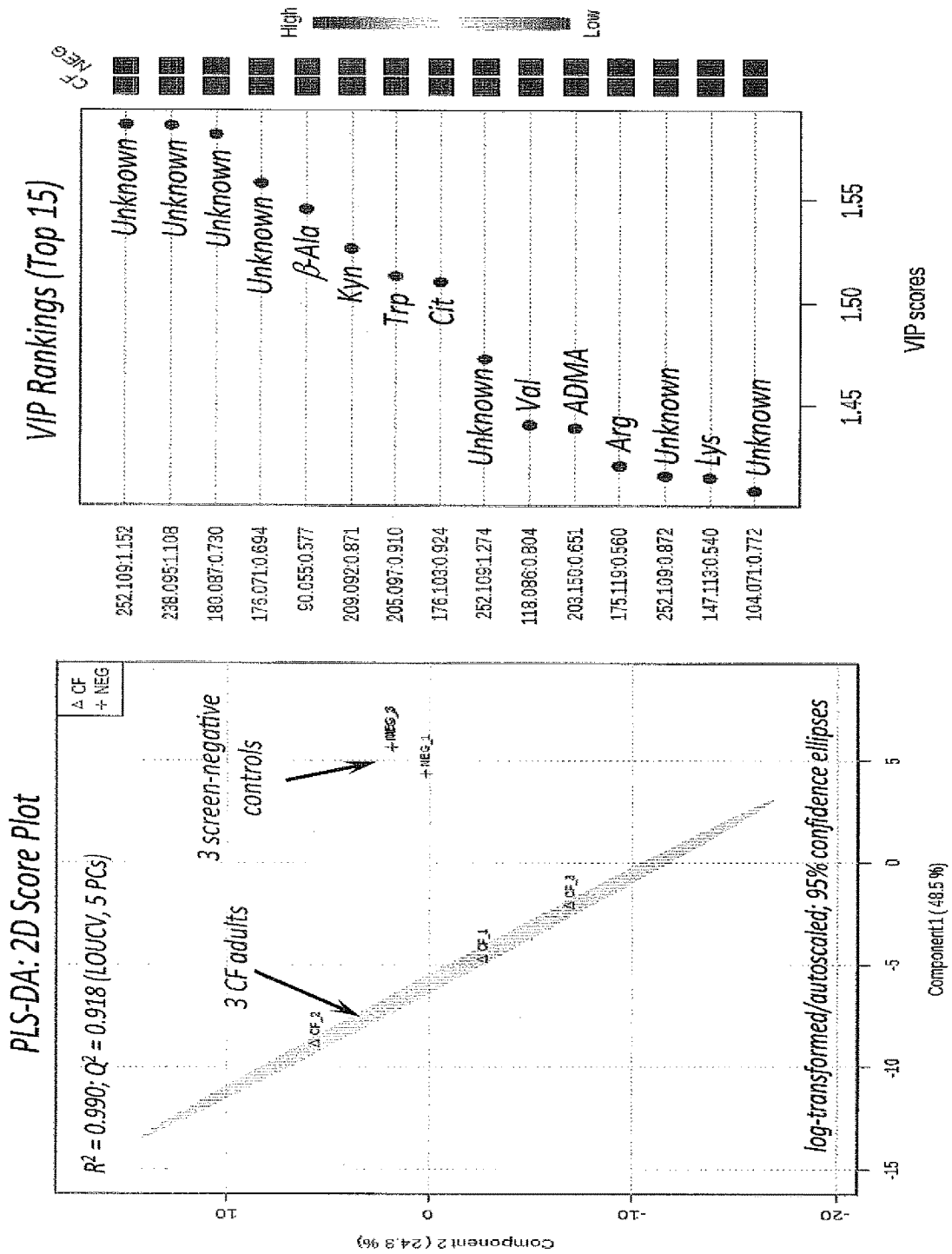
FIG. 7 depicts multivariate statistical analysis of 82 authentic metabolites measured in dried blood spot (DBS) extracts by MSI-CE-MS for the discovery of putative markers differentially expressed in affected CF adults (n=3) relative to healthy controls (n=3) when using (a) a 2D scores plot in partial-least squares discriminate analysis (PLS-DA) with markers annotated by their variable importance in projection (VIP) ranking and (b) receiver operating characteristic (ROC) curves for single or ratiometric CF-specific markers.

FIG. 7 depicts multivariate statistical analysis of 82 authentic metabolites measured in dried blood spot (DBS) extracts by MSI-CE-MS for the discovery of markers differentially expressed in affected CF adults (n=3) relative to healthy controls (n–3) when using (a) a 2D scores plot in partial-least squares discriminate analysis (PLS-DA) with markers annotated by their variable importance in projection (VIP) ranking and (b) receiver operating characteristic (ROC) curves for single or ratiometric CF-specific markers. Excellent discrimination of adults with CF from healthy controls was feasible when analyzing a panel of polar metabolites derived from methanol-based dried blood spot extracts with good accuracy ($R^2=0.999$) and robustness ($Q^2=0.675$) when using leave-one-out-at-a-time cross-validation. The VIP ranking summarizes the most significant metabolites associated with CF based on their measured normalized responses after log-transformation and auto-scaling, such as two metabolites, one with a m/z of 252.109 and a RMT of 1.152, and another with a m/z 238.095 and a RMT of 1.108 (both lower in CF), as well as β-alanine and L-kynurenine (both higher in CF). Alternatively, ROC curves can be used to select and rank CF-specific markers based on their ability to classify infants with CF with high sensitivity and specificity (in both cases area under the curve, AUC>1.00) based on an optimum threshold cut-off value, including single and ratiometric markers, such as the metabolite with a m/z of 238.095 and a RMT of 1.108 and L-citrulline:metabolite (m/z of 238.095) ratio, respectively. Metabolites that have a high AUC value, a high average fold-change and/or a low p-value are considered markers for CF screening.

FIG. 8 depicts a strategy for structural elucidation of metabolites differentially expressed in dried blood spot extracts from CF subjects using accurate mass, spiking with authentic standards and tandem MS (MS/MS), such as a metabolite with a m/z of 238.095 [MH$^+$] and a RMT of 1.108. In this case, the accurate mass of the ion corresponds to three putative molecular formulae, whereas the highest ranked molecular formula is associated with 229 possible chemical structures/isomers based on $C_9H_{11}N_5O_3$. A database search (e.g., Human Metabolome Database) for the ion was biopterin as a putative chemical structure among several other isomers and isobars. However, spiking of biopterin available as a purified chemical standard into the dried blood sample extract resulted in its migration after the ion (m/z of 238.095 [MH$^+$]) since it has a characteristic RMT of 1.108. In addition, a comparison of tandem (MS/MS) spectra confirmed that biotperin did not correspond to the ion given the different fragment ions generated upon collision-induced dissociation and their relative intensities. Thus, identification of metabolite markers of CF may be determined by matching of RMT and MS/MS spectra with authentic chemical standards.

Figure 9:
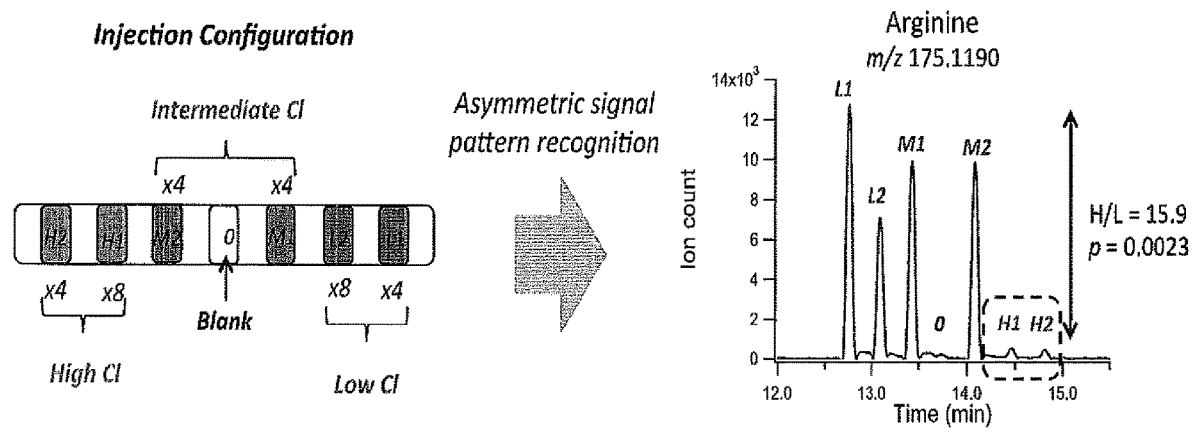
FIG. 9 (a) illustrates an asymmetric signal pattern recognition for L-arginine using MSI-CE-MS when comparing pooled sweat specimens from screen-positive infants and (b) demonstrates a sub-group comparison of metabolites associated with the urea cycle/nitric acid pathway differentially expressed in pooled sweat specimens from screen-positive CF infants with low (<30 mM), intermediate (30-59 mM) and high (>60 mM) sweat chloride results indicative of L-arginine deficiency for affected CF infants.
Figure 9:
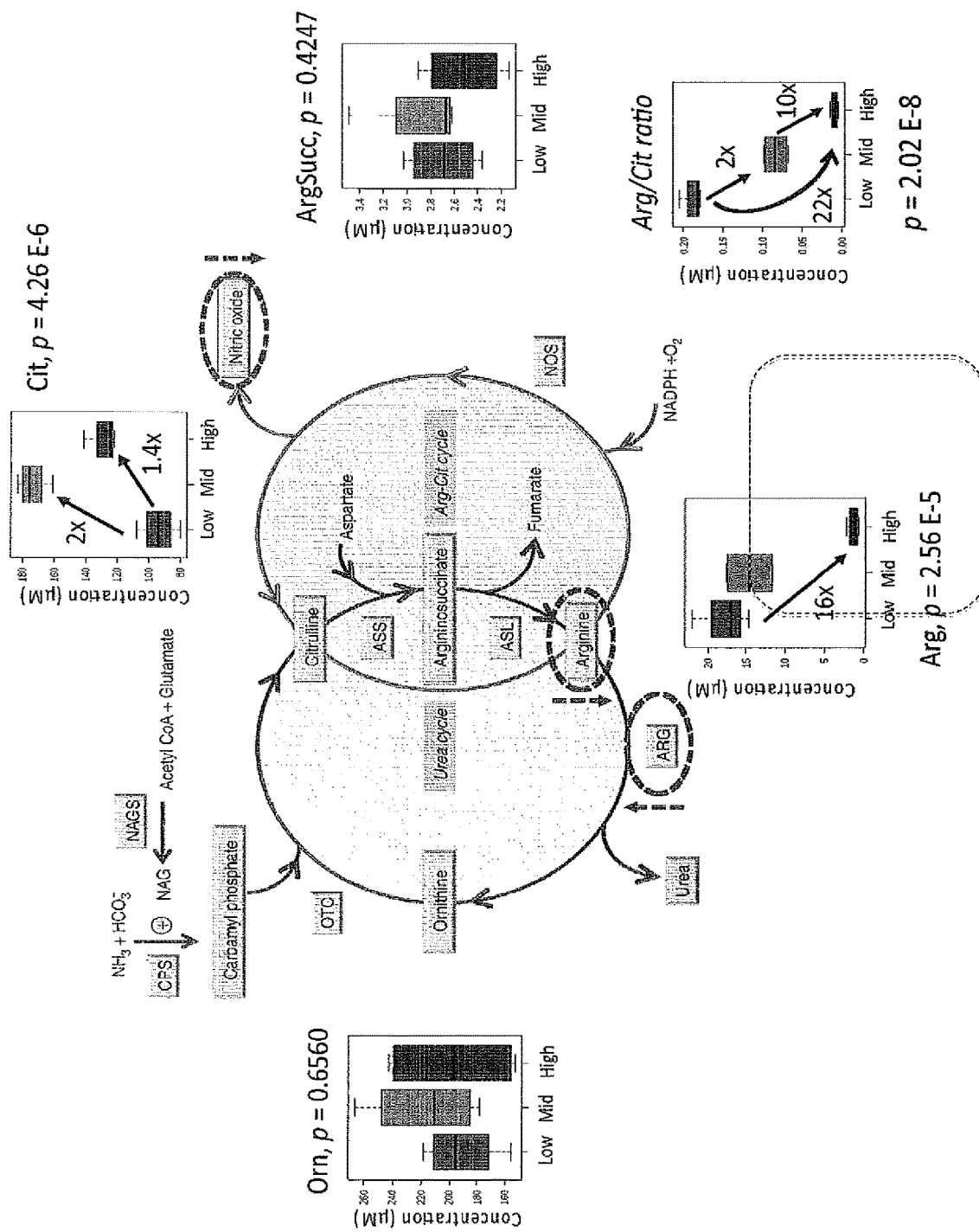

FIG. 9 demonstrates a sub-group comparison of metabolites associated with the urea cycle/nitric acid pathway differentially expressed in pooled sweat specimens from screen-positive CF infants with low (<30 mM), intermediate (30-59 mM) and high (>60 mM) sweat chloride results indicative of L-arginine deficiency for affected CF infants. Two specific metabolites in the urea cycle/NO biosynthesis were associated with CF subjects, including L-arginine and L-citrulline, as well as their ratio (Arg/Cit). In contrast, L-ornithine and L-argininosuccinate do not exhibit a statistical significant difference in pooled sweat specimens from affected infants (i.e., high or intermediate sweat chloride) and unaffected carriers (i.e., low sweat chloride). Arginine deficiency is evident in infants with classic CF as demonstrated in the asymmetric signal pattern recognition for L-arginine (an ion with a 175.119 m/z and a RMT of 0.560) using MSI-CE-MS when comparing pooled sweat specimens from screen-positive infants with different categories of sweat chloride results.

Figure 10:
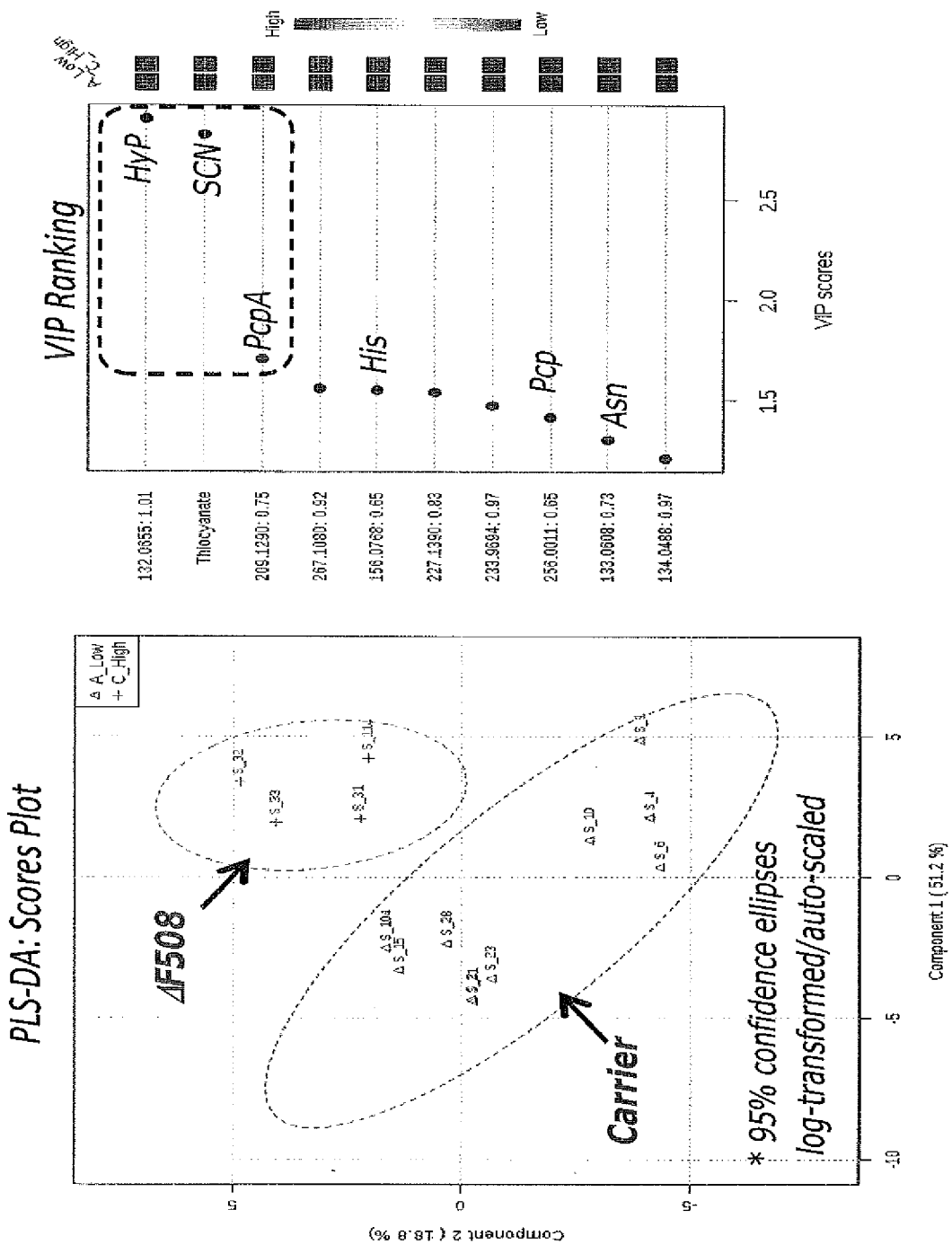
FIG. 10 depicts multivariate statistical analysis of 75 authentic metabolites measured in pilocarpine-stimulated sweat specimens by MSI-CE-MS for the discovery of markers differentially expressed in affected infants with classic CF (n=4, heterozygotes with delF508 CFTR mutation with a high sweat chloride result >60 mM) relative to screen-positive/unaffected carriers (n=10 with a low sweat chloride result <30 mM) when using (a) a 2D scores plot in partial-least squares discriminate analysis (PLS-DA) with markers annotated by their variable importance in projection (VIP) ranking and (b) receiver operating characteristic (ROC) curves for ratiometric CF-specific markers detected in residual sweat specimens; and (c) illustrates the conversion of pilocarpine to pilocarpic acid.
Figure 10:
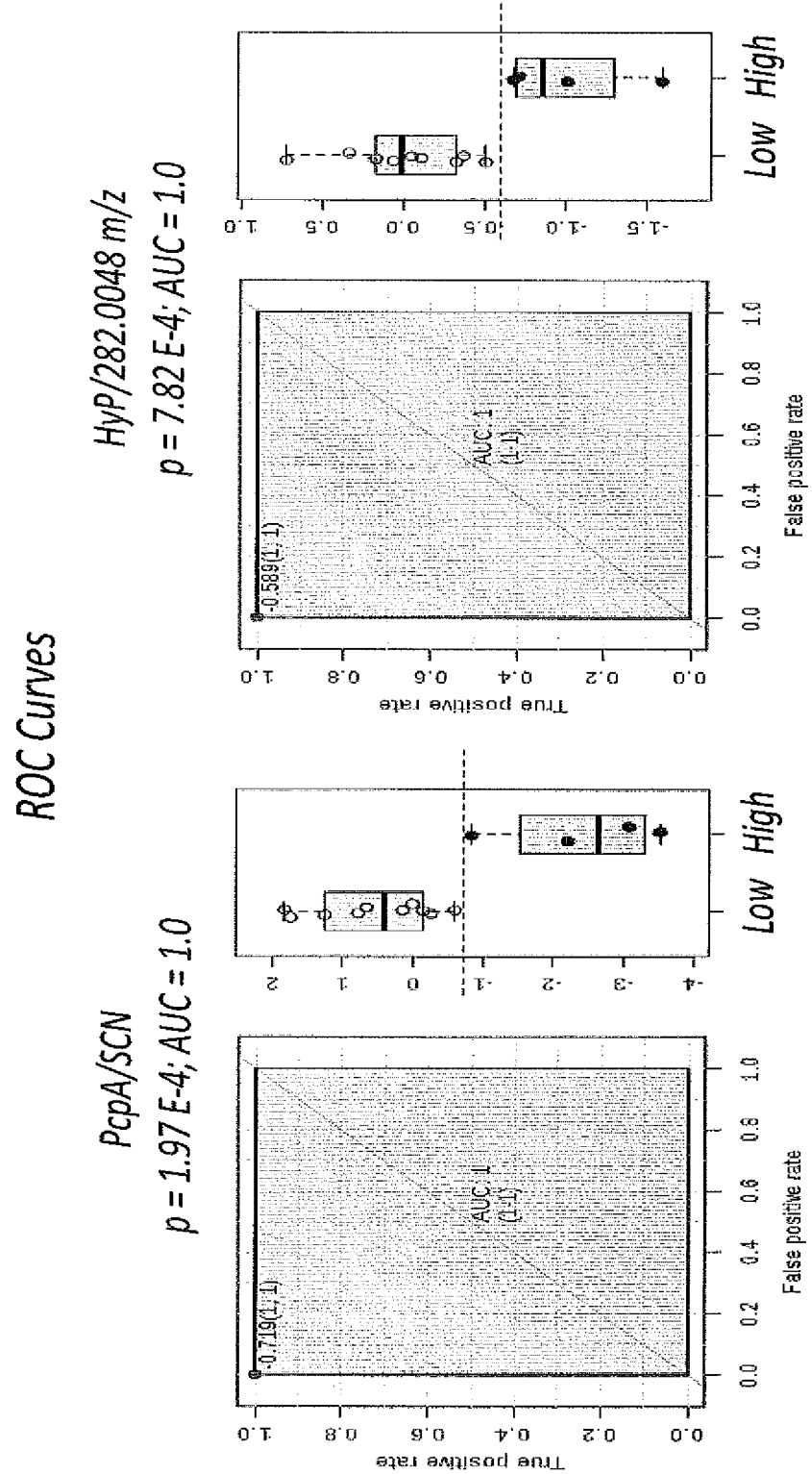
Figure 10:
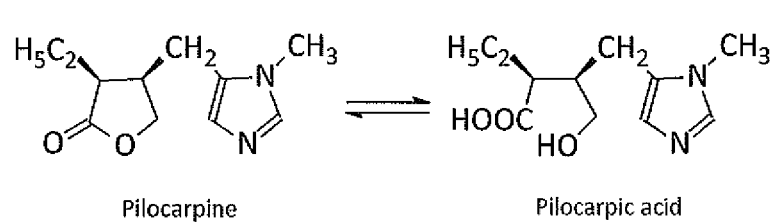

FIG. 10 depicts multivariate statistical analysis of 75 authentic metabolites measured in pilocarpine-stimulated sweat specimens by MSI-CE-MS for the discovery of putative markers differentially expressed in affected infants with classic CF (n=4, heterozygotes with delF508 CFTR mutation with a high sweat chloride result >60 mM) relative to screen-positive/unaffected carriers (n=10 with a low sweat chloride result <30 mM) when using (a) a 2D scores plot in partial-least squares discriminate analysis (PLS-DA) with markers annotated by their variable importance in projection (VIP) ranking and (b) receiver operating characteristic (ROC) curves for single or ratiometric CF-specific markers detected in residual sweat specimens. The VIP ranking summarizes the most significant metabolites associated with CF based on their measured normalized responses after log-transformation and autoscaling, such as thiocyanate (SCN) and a metabolite with a m/z of 267.129 and a RMT of 0.750 (both lower in classic CF with high sweat chloride), as well as 3-hydroxy-L-proline (HyP) and pilocarpic acid (PcpA) (both higher in CF with high sweat chloride). Alternatively, ROC curves can be used to select and rank CF-specific markers based on their ability to classify infants with CF with high sensitivity and specificity (in both cases area under the curve, AUC >1.00) based on an optimum threshold cut-off value, such as ratiometric markers, including PcpA/SCN and HyP/metabolite (with a m/z of 282.005). Metabolites that have a high AUC value, a high average fold-change and/or a low p-value are considered markers for CF screening.

Figure 11:
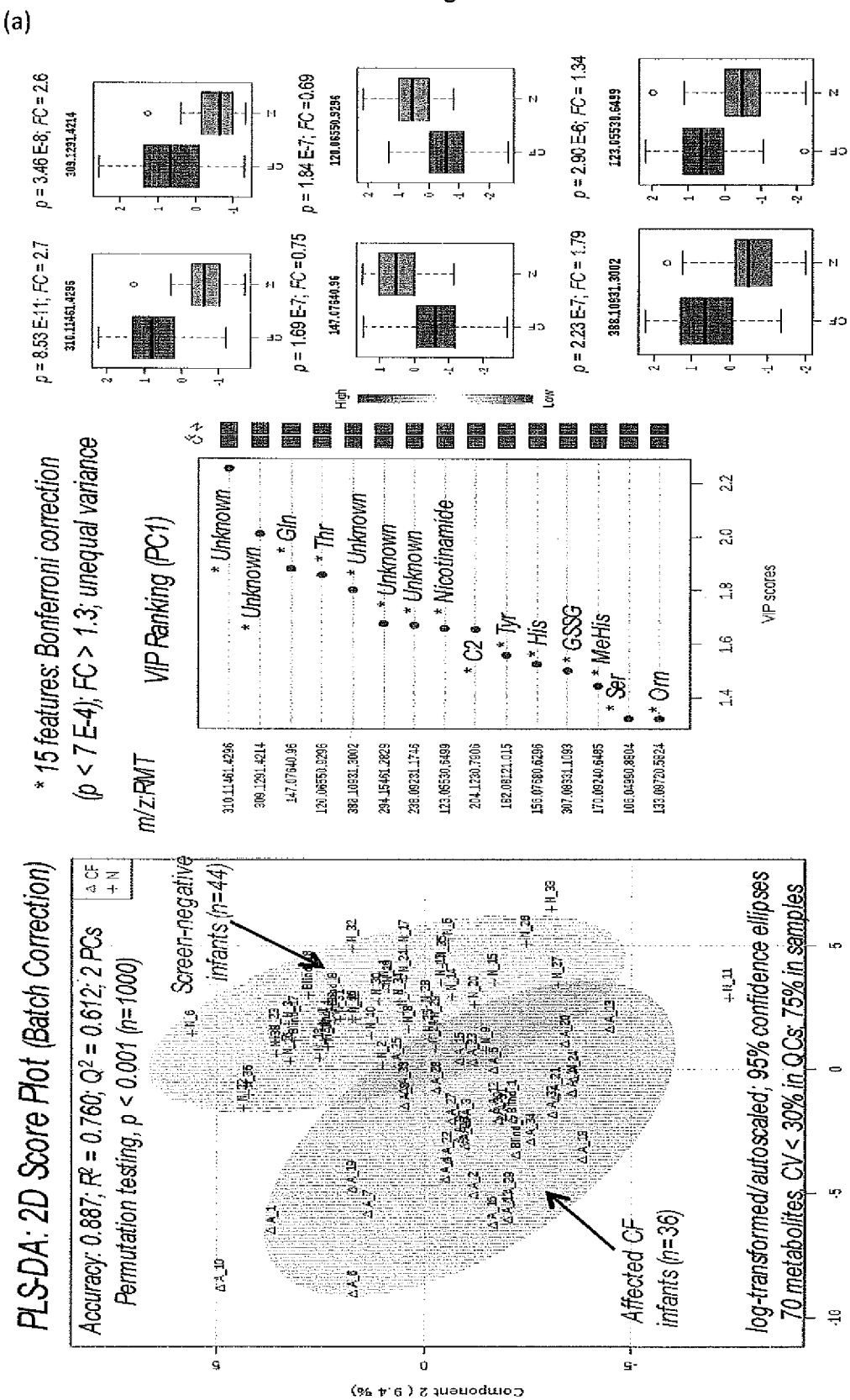
FIG. 11 depicts multivariate statistical analysis for classifying a panel of metabolites that are differentially expressed in affected/screen-positive CF newborn infants (n–36) relative to healthy/screen-negative controls (n=44) from 70 polar metabolites measured in retrospective dried blood spot (DBS) specimens by MSI-CE-MS when using (a) a 2D scores plot in partial-least squares discriminate analysis (PLS-DA) with biomarkers (metabolites with known and unknown chemical structures) annotated by their m/z:RMT using variable importance in projection (VIP) ranking and box plots highlighting the most significant metabolites in terms of average fold-change (FC) and statistical significance (p-value), as well as (b) receiver operating characteristic (ROC) curves for single or ratiometric CF-specific markers.
Figure 11:
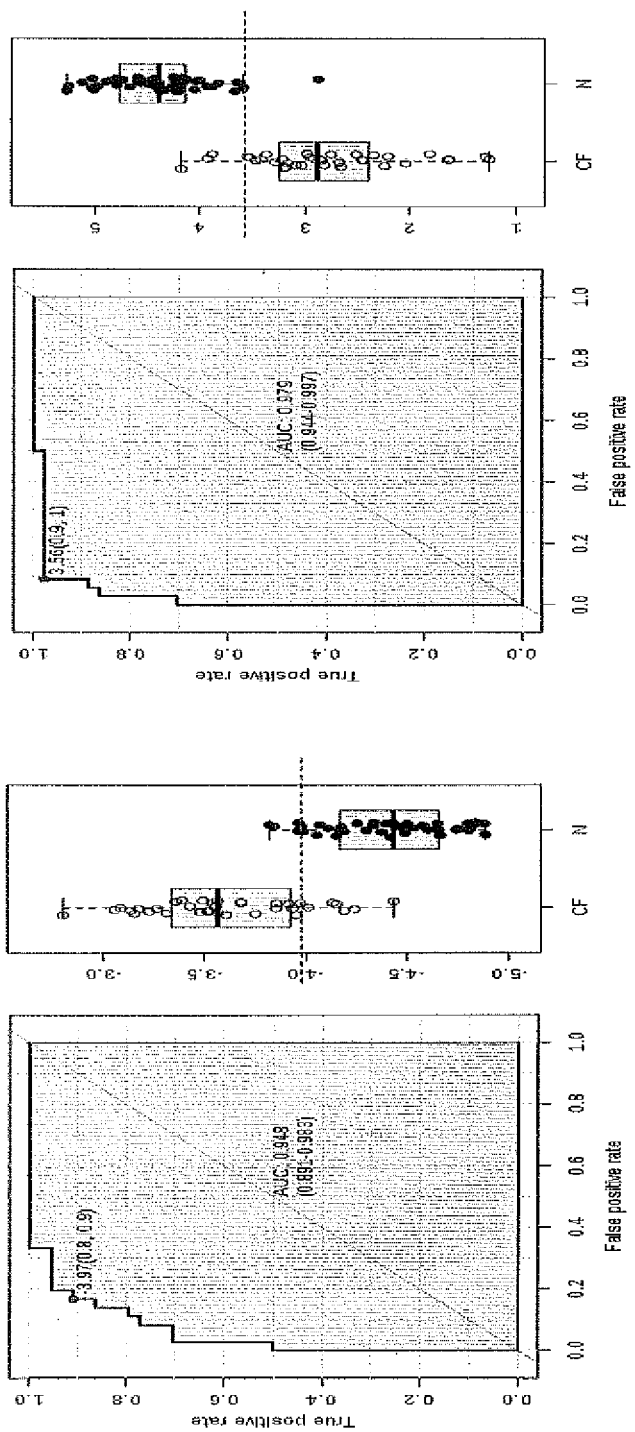

FIG. 11 shows an expanded analysis of retrospective DBS extracts from a large number of CF infants (category A with high sweat chloride, n=36) and healthy/screen-negative infants (n=44) when using MSI-CE-MS. In both groups, infants were normal birth weight and gender-balanced and CF infants (2 days old) had no apparent signs of the disease. In this case, up to 15 metabolites were shown to be differentially expressed in DB S extracts even after Bonferroni correction for multi-hypothesis testing, including metabolites that were originally discovered in the earlier study (FIG. 6), such as Gln, GSSG and an unknown ion 238 m/z, as well as metabolites, including Thr, Tyr, O-acetyl-L-carnitine (C2), His, MeHis, Ser and Orn. Additionally, several unknown metabolites were also shown to be differentially expressed between affected CF infants and healthy controls as depicted in FIG. 11 (a) a 2D scores plot in partial-least squares discriminate analysis (PLS-DA) with markers annotated by their variable importance in projection (VIP) ranking and (b) receiver operating characteristic (ROC) curves for single or ratiometric CF-specific markers detected in residual sweat specimens. Overall, the unknown ion (m/z:RMT, 310.115:1.43) was consistently found to be the most significant metabolite that was elevated about 2.7-fold in CF infants (p=8.53 E-11) relative to healthy controls that also has a high AUC=0.898 that was further improved in ROC curves as a ratiometric marker (His/310 m/z) with sensitivity and selectivity of 90% and 100%, respectively.

Discussion

Herein is reported for the first time an untargeted metabolomic study of DBS extracts (i.e., whole blood specimens), as well as residual sweat samples from screen-positive infants for the determination of novel metabolite signatures indicative of CF. The major aim of metabolomics is to measure statistically different metabolite responses between two or more sample cohorts (e.g., healthy/disease) based on their measured signal intensities when using nuclear magnetic resonance (NMR) or MS when coupled to various separation techniques (Kuehnbaum and Britz-McKibbin *Chem. Rev.* 2013, 113: 2437). Complementary multivariate statistical methods were then used to reduce data dimensionality and noise while ranking a sub-set of molecular features (i.e., metabolites) that are associated with group classification (Kuehnbaum et al. *Sci. Reports* 2014, 4: 6166). Nevertheless, a major trade-off of separations is the low sample throughput associated with solute elution and column pre-conditioning when using conventional GC, LC and/or CE-MS methods. Also, traditional data workflows in metabolomics require complicated data pre-processing algorithms to peak pick and align data that are time-consuming and prone to bias. In the present case, multi-segment injection-capillary electrophoresis-mass spectrometry (MSI-CE-MS) was used as a high-throughput screening platform (Kuehnbaum et al. *Anal. Chem.* 2013, 85: 10664) in metabolomics for biomarker determination that is applicable to characterization of volume-restricted samples from biorepositories (Nori de Macedo et al. *Anal. Chem.* 2014, 86: 10010).

FIG. 2 highlights that seven or more sample segments can be serially injected into a single capillary to improve sample throughput up to one order of magnitude while retaining good separation efficiency, selectivity, desalting and quantitative performance prior to electrospray ionization (ESI)-MS. A major advantage of MSI-CE-MS is the increased sample throughput and data quality that is achieved via serial injection of multiple sample plugs within the same separation, including different biological samples from individual subjects and reference/quality controls (Kuehnbaum et al. *Anal. Chem.* 2013, 85: 10664). This method was used to identify CF-specific markers in volume-restricted biological samples from affected CF infants and adults, including dried blood spot extracts and pilocarpine-stimulated sweat specimens. Indeed, residual sweat samples stored after sweat chloride measurements for confirmatory diagnosis of CF often contains less than 5 µL volume for subsequent analysis.

FIG. 3 shows that a wide range of polar/ionic metabolites can be analyzed from dried blood spot extracts when using CE-MS (Chalcraft and Britz-McKibbin *Anal. Chem.* 2009, 81: 307), including primary or ratiometric markers associated with amino acid, fatty acid and organic acid disorders relevant to newborn screening programs (e.g., amino acids and acylcarnitines). This was first performed in order to rigorously validate the specificity, precision and accuracy of MSI-CE-MS based on known markers (e.g., primary, secondary or ratiometric markers) for different in-born errors of metabolism, such as elevated L-phenylalanine (Phe >120 µM) or L-phenylalanine:L-tyrosine ratio (Phe/Tyr >3) in dried blood spot extracts that are indicative of phenylketonuria (PKU).

FIG. 4 provides an overview of the data workflow in metabolomics for biomarker discovery that relies on unsupervised (e.g., principal component analysis, hierarchical cluster analysis) and supervised multivariate statistical methods (e.g., partial least squares-discriminate analysis, receiver operating characteristic curves) to reduce data dimensionality in metabolomics and classify sub-groups of subjects based on statistically significant molecular features (Kuehnbaum et al. *Electrophoresis* 2015, doi: 10.1002/elps.201400604) related to CF in affected subjects as defined by their characteristic mass-to-charge ratio and relative migration time (m/z:RMT). These putative lead candidates were then identified by comparison with MS/MS spectral databases and co-migration after spiking with authentic standards followed by their accurate quantification.

An asymmetric signal pattern recognition strategy was applied when using MSI-CE-MS in order to unambiguously identify CF-specific metabolite signatures relative to healthy and disease controls. FIG. 5 depicts three pairs of proficiency DBS samples from the Centres for Disease Control (CDC) that were simultaneously analyzed by MSI-CE-MS. Duplicate extractions were analyzed for six different IEM while including a healthy control as reference. Serial injection of a specific dilution pattern for each pair of samples thus facilitated sample identification while providing greater quality fidelity. For instance, a statistically significant elevation of L-phenylalanine (Phe) is indicative of PKU (i.e., second pair of samples injected) in contrast to other primary markers for IEM, such as L-tyrosine (Tyr) where ion peak intensities derived from all samples were not significantly different (i.e., no evidence of tyrosinemia). This approach was then validated for four other IEM with known primary or secondary markers from DBS extracts, including medium-chain acyl-coenzyme A dehydrogenase deficiency (MCADD), glutaric academia (type 1), maple syrup urine disease, and citrullinemia (data not shown). A similar approach was adopted for analysis of DBS samples from three adult CF patients when using an untargeted metabolomics workflow in MSI-CE-MS (FIG. 4) in order to identify CF-specific markers. In this case, a total of up to 82 cationic metabolites from DBS extracts and 75 cationic and anionic metabolites in sweat specimens were analyzed by MSI-CE-MS with adequate precision (CV<30%) that was not detected in sample blanks.

Univariate statistical methods were used to rank metabolites differentially expressed between CF patients and healthy controls when using a student's t-test based on the average fold-change (FC) in measured ion responses and its significance level (p-value) for each metabolite. Table 1 summarizes twenty-one metabolites in methanol-derived dried blood spot extracts that were found to be statistically different in infant and/or adult CF patients (p<0.05) relative to healthy controls, including several metabolites as defined by their characteristic m/z:RMT. CF-specific markers were derived from metabolic pathways associated with tryptophan/kynurenine pathway (e.g., L-tryptophan, L-kynurenine), glutaminolysis/ammonia transport (e.g., L-glutamine), urea cycle/nitric oxide biosynthesis (e.g., L-citrulline, L-arginine), oxidative stress (e.g., oxidized glutathione disulfide, L-proline), lysine catabolism/carnitine biosynthesis (L-lysine, L-carnitine), branched chain amino acids (e.g., L-valine), mitochondrial β-oxidation (O-butyryl-L-carnitine) and protein turn-over (e.g., 3-hydroxy-L-proline).

controls (n=3). In this case, adult CF patients were readily distinguished from healthy controls on the same plot when using the first two principal components (PCs) representing about 73% of the explained data variance. FIG. 7a shows that each CF subject can be readily distinguished based on their characteristic metabolic phenotype that likely reflects their underlying disease phenotype heterogeneity and differential responses to therapy over a lifetime.

In addition, initial characterization of the sweat metabolome from affected CF infants was performed by MSI-CE-MS relative to unaffected screen-positive carriers. Indeed, this work represents the first reported study in metabolomics using authentic neonate sweat specimens collected by pilocarpine iontophoresis (Calderon-Santiago et al. *J Chromatogr A* 2014,1333: 70). A major advantage of this work is the ability to directly analyze volume-restricted biofluids ($\approx$3-5 µL) after chloride sweat testing without complicated sample workup. Over 80 cationic and anionic metabolites have been identified in pooled sweat samples when using a

TABLE 1

TOP 21 Putative CF-Specific Markers in Dried Blood Spot Extracts

| Name | Metabolite (m/z:RMT) | p-value Significance | Fold-change CF/Normal | Metabolic Pathway |
|---|---|---|---|---|
| 1. L-Tryptophan (Trp) | 205.097:0.910 | 1.89E−03 | 2.05 | Trptophan/kynurenine pathway |
| 2. L-Citrulline (Cit) | 176.103:0.924 | 3.04E−03 | 1.4 | Urea cycle/NO biosynthesis |
| 3. Unknown | 238.095:1.108 | 4.34E−03 | 0.0363 | — |
| 4. Unknown | 180.087:0.730 | 4.75E−03 | 0.159 | — |
| 5. Unknown | 252.109:1.274 | 5.58E−03 | 0.471 | — |
| 6. Unknown | 298.053:0.794 | 5.90E−03 | 0.1 | — |
| 7. L-Glutamine (Gln) | 147.076:0.894 | 6.29E−03 | 0.59 | Glutaminolysis/Ammonia transport |
| 8. Unknown | 252.109:1.152 | 8.50E−03 | 0.0202 | — |
| 9. Unknown | 176.071:0.694 | 9.10E−03 | 1.97 | — |
| 10. Oxidized glutathione (GSSG) | 307.083:1.044 | 1.18E−02 | 0.656 | Oxidative stress |
| 11. Beta-Ala | 90.055:0.562 | 1.23E−02 | 1.66 | Carnosine catabolism |
| 12. L-Proline (Pro) | 116.071:0.887 | 1.42E−02 | 0.774 | Oxidative stress |
| 13. L-Ornithine (Orn) | 133.097:0.538 | 1.87E−02 | 2.35 | Urea cycle/NO biosynthesis |
| 14. Unknown | 104.071:0.772 | 2.21E−02 | 2.01 | — |
| 15. O-Butyryl-L-Carnitine (C4) | 232.154:0.758 | 3.22E−02 | 0.402 | Acylcarnitine/Beta-oxidation |
| 16. L-Arginine (Arg) | 175.119:0.560 | 3.63E−02 | 0.527 | Urea cycle/NO biosynthesis |
| 17. Unknown | 252.109:0.872 | 3.70E−02 | 0.644 | — |
| 18. L-Valine (Val) | 118.0863:0.804 | 3.94E−02 | 1.81 | Branched-chain amino acid |
| 19. L-Carnitine (C0) | 162.112:0.679 | 3.95E−02 | 1.28 | Acylcarnitine/Beta-oxidation |
| 20. L-Kynurenine (Kyn) | 209.092:0.871 | 4.04E−02 | 0.63 | Trptophan/kynurenine pathway |
| 21. L-Lysine (Lys) | 147.113:0.523 | 4.14E−02 | 2.89 | Lysine catabolism/carnitine biosynthesis |

\* tentative identification based on database match, whereas all other metabolites were identified with authentic chemical standards In addition, complementary multivariate statistical methods were also applied to identify and rank CF-specific metabolites in dried blood spot extracts. FIG. 6a depicts a 2D scores plot after partial-least squares-discriminant analysis (PLS-DA) and log-transformation and autoscaling of the data matrix consisting from four affected CF infants (n=4) relative to a screen-negative/healthy infants (n=4) in dried blood spot extracts. Affected CF infants confirmed with high sweat chloride (>60 mM) were readily distinguished from healthy controls on the same plot when using the first two principal components (PCs) representing about 54% of the explained data variance. FIG. 6a shows that each CF subject can be readily distinguished from each other based on their characteristic metabolic phenotype that likely reflects their underlying disease phenotype heterogeneity.

Similarly, FIG. 7a depicts a 2D scores plot after partial-least squares-discriminant analysis (PLS-DA) after log-transformation and autoscaling of the data matrix consisting from three adult CF patients (n=3) relative to healthy dilution trend filter in MSI-CE-MS (Kuehnbaum et al. *Anal. Chem.* 2013, 85: 10664) to reject biochemical/chemical noise while authenticating metabolites based on three criteria to reduce false discoveries, namely a reproducible signal (CV<30%) undergoing a linear decrease in response ($R^2$>0.900) that lacks a blank signal. Amino acids, biogenic amines, organic acids and various other classes of metabolites were confirmed in pooled sweat samples, including pilocarpine (Pcp) and preservatives (e.g., methylparaben) from the gel disk, as well as a blue dye (i.e., Brilliant Blue FCF) used to visualize sweat collection in tubes. Three sub-sets of sweat samples were initially pooled together from screen-positive CF infants having low (<30 mM), intermediate (30-59 mM) and high (>60 mM) sweat chloride test results. Differentially expressed metabolites between the three sweat sub-groups were identified by MSI-CE-MS for biomarker discovery based on asymmetric signal pattern recognition. One of the most significant findings was the discovery of alterations in sweat metabolites associated with urea cycle/nitric oxide pathway as reflected by L-arginine (Arg) depletion and lower Arg/L-citrulline (Arg/Cit) ratios in infants with high sweat chloride associated with classic CF who are frequently compound heterozygotes with a single del508 mutation for CFTR as shown in FIG. 9. Indeed, these results are consistent with findings from dried blood spot extracts.

Untargeted metabolite profiling of sweat specimens from a group of screen positive CF infants with normal sweat chloride (i.e., unaffected carriers <30 mM) relative to four CF infants with high sweat chloride (i.e., affected CF infants >60 mM) in FIG. 10 shows clear group classification as reflected by the 2D scores plots when using partial least squares-discriminate analysis (PLS-DA). As expected, CF-affected infants had elevated levels of thiocyanate (SCN) present in sweat (Gibbs and Hutchings *Proc Soc Exp Biol Med.* 1961,106: 368), but also higher levels of a number of other compounds as summarized Table 2, such as 3-hydroxy-L-proline (Hyp), as well as pilocarpic acid (PcpA)—the latter compound is a major metabolite of pilocarpine (Pcp) that was not detected in used gel pads after iontophoresis.

amino acids and protein turn-over. Relevant portions of references referred to herein are incorporated by reference.

EXAMPLE 2

Determination of Predictive Biomarkers Associated With Affected Infants With Cystic Fibrosis An extensive analysis of over 150 retrospective dried blood spot (DBS) specimens from Newborn Screening Ontario was completed with adequate statistical power to confirm earlier preliminary results, including screen-negative (healthy infants, n=44), confirmed CF cases (n=36, category A), as well as screen-positive/unaffected carriers (n=72). The latter group is associated with category B and C screen-positive cases that are responsible for a large fraction (80-85%) of screen-positive cases that proceed for confirmatory sweat chloride testing, the majority of which are unaffected infants with low sweat chloride results despite having a known CFTR mutation (i.e., carrier of a single mutation). The methods used were are described in Example 1 for dried blood spot specimens.

TABLE 2

| TOP 21 Putative CF-Specific Markers in Pilocarpine-stimulated Sweat | | | Fold-change | |
| --- | --- | --- | --- | --- |
| Name | Metabolite (m/z:RMT) | p-value Significance | CF/Screen-negative | Metabolic Pathway |
| 1. Unknown* | 280.078:0.967 | 1.18E−09 | 0.00331 | — |
| 2. Unknown* | 115.040:1.076 | 8.07E−08 | 2.68 | — |
| 3. L-Citrulline (Cit) | 176.103:0.924 | 4.26E−06 | 1.86 | Urea cycle/NO biosynthesis |
| 4. Pilocarpic acid (PcpA) | 227.139:0.794 | 4.54E−06 | 3.25 | Hydrolysis product of drug stimulant (Pcp) |
| 5. Unknown* | 160.062:0.917 | 7.49E−06 | 2.54 | — |
| 6. 3-Hydroxy-L-Proline (Hyp) | 132.066:1.024 | 1.51E−05 | 2.95 | Oxidative stress/collagen turn-over |
| 7. L-Arginine (Arg) | 175.119:0.560 | 1.03E−04 | 0.0629 | Urea cycle/NO biosynthesis |
| 8. Unknown* | 201.077:0.840 | 3.37E−05 | 2.1 | — |
| 9. Unknown* | 129.056:1.019 | 1.03E−04 | 1.68 | — |
| 10. L-Tyrosine (Tyr) | 182.081:0.952 | 1.64E−04 | 1.79 | Aromatic amino acid biosynthesis |
| 11. Unknown* | 257.114:0.835 | 3.41E−04 | 1.32 | — |
| 12. L-Phenylalanine (Phe) | 166.086:0.917 | 3.95E−04 | 1.8 | Aromatic amino acid biosynthesis |
| 13. Unknown | 235.118:0.768 | 7.16E−04 | 2.05 | — |
| 14. Hypoxanthine (HyX) | 137.046:1.087 | 1.76E−03 | 0.35 | Purine degradation pathway |
| 15. Unknown | 194.138:0.721 | 1.94E−03 | 1.52 | — |
| 16. Unknown | 370.053:0.820 | 3.08E−03 | 1.56 | — |
| 17. Pilocarpine (Pcp) | 209.129:0.713 | 3.08E−04 | 1.56 | Drug stimulant for sweat |
| 18. Unknown | 247.037:0.565 | 9.36E−04 | 1.55 | — |
| 19. Unknown | 139.050:0.686 | 1.23E−02 | 1.8 | — |
| 20. L-Lysine (Lys) | 147.113:0.523 | 1.35E−02 | 2.21 | Lysine catabolism/carnitine biosynthesis |
| 21. Unknown | 280.024:0.687 | 1.46E−02 | 1.62 | — |

*unknown molecular features detected under negative ion mode instead of positive ion mode conditions This preliminary data clearly highlights the wealth of "value-added" biochemical insights derived from secondary use of sweat beyond chloride that is needed for improved assessment of normal or indeterminate sweat chloride test results with ambiguous diagnoses despite having one or two CFTR mutations as in the case of CFTR-related metabolic disorder.

A panel of metabolites differentially expressed in adult/infant CF patients has been determined when analyzing both dried blood spot extracts and pilocarpine-stimulated sweat specimens. Multi-segment injection-capillary electrophoresis-mass spectrometry in conjunction with multivariate statistical methods was used for the identification of a panel of metabolites expressed in affected CF subjects that were associated with aberrant urea cycle/NO biosynthesis, tryptophan catabolism/kynurenine pathway, lysine catabolism/carnitine biosynthesis, fatty acid β-oxidation/branched chain The following biomarkers in DBS extracts were identified and further validated in a larger cohort of samples for improved population-based screening of affected CF infants, which correspond with those identified as set out in Example 1: L-glutamine, L-proline, L-ornithine, L-arginine, glycine, oxidized glutathione disulfide (GSSG), hypoxanthine and an ion denoted by its characteristic mass-to-charge and relative migration time (m/z:RMT) of 238.095:1.175 (MH$^+$, $C_9H_{11}N_5O_3$). In addition, several other metabolites were found to be significant as differentiating metabolites from DBS extracts in authentic CF infants that were not originally reported, including O-acetyl-L-carnitine, 2-aminobutyric acid, betaine glycine, γ-butyrobetaine (deoxy-L-carnitine), 3-methyl-L-histidine, guanosine, creatine, L-histidine, nicotinamide, L-serine, L-tyrosine, and L-threonine, as well as several ions as denoted by their characteristic m/z:RMT, charge state for ion (e.g., MH$^+$) and most likely molecular formula as measured by CE-ESI-MS, including 186.088: 0.989 (MH$^+$; C$_7$H$_{11}$N$_3$O$_3$), 290.135:1.225 (MH$^+$; C$_{11}$H$_{19}$N$_3$O$_6$), 294.156:1.225 (MH$^+$; C$_{13}$H$_{19}$N$_5$O$_3$), 310.114:1.430 (MH$^+$; C$_{12}$H$_{15}$N$_5$O$_5$), 309.129:1.283 (MH$^+$; C$_{11}$H$_{20}$N$_2$O$_8$), 388.109:1.300 (M+2H$^{2+}$; C$_{26}$H$_{42}$N$_6$O$_{17}$S$_2$), and 445.139:1.325 (MH$^+$; C$_{18}$H$_{28}$N$_4$O$_3$S$_3$).

Figure 12:
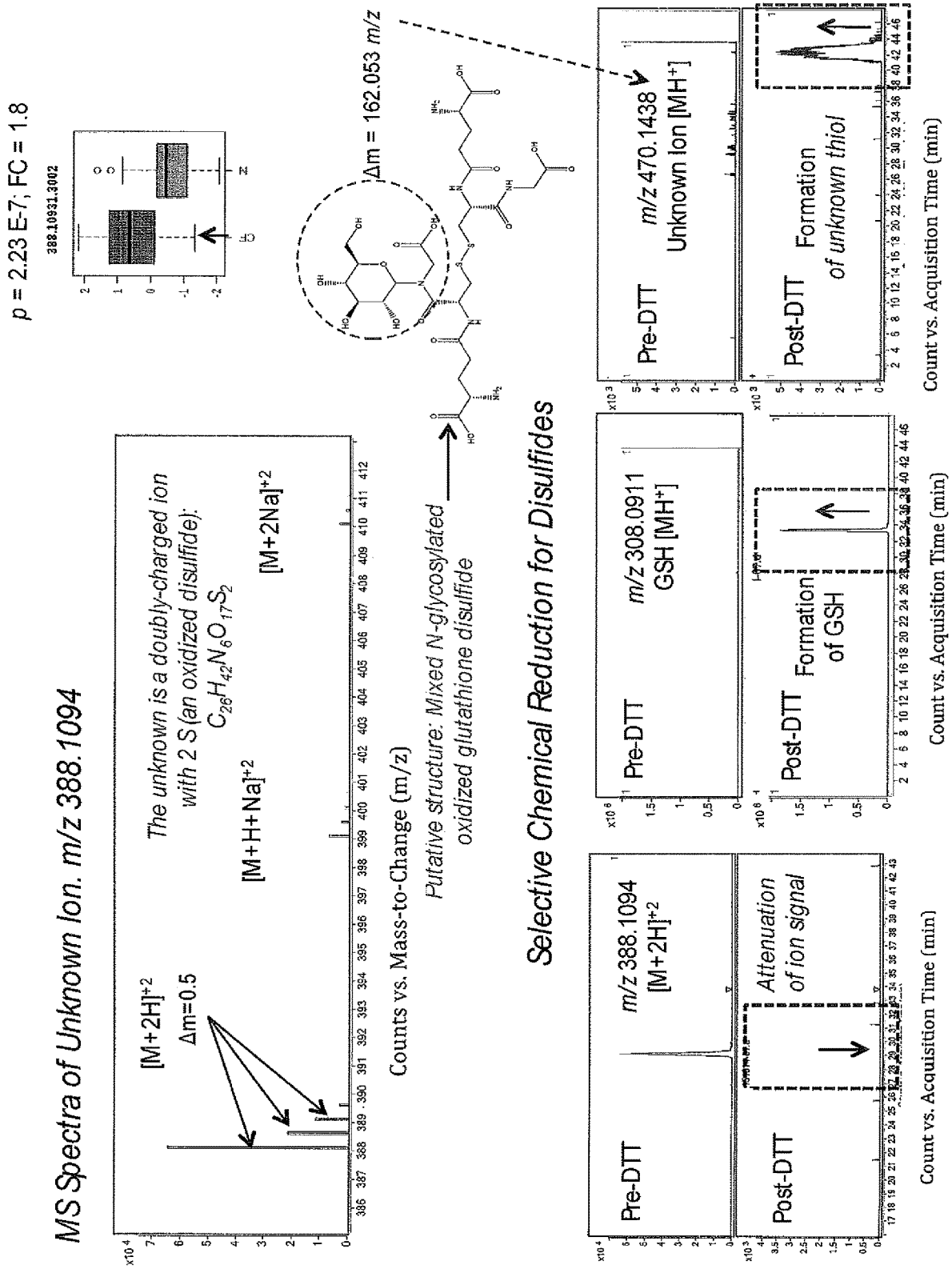
FIG. 12 depicts a strategy for de novo structural elucidation of metabolites of clinical significance as putative biomarkers of CF in affected infants when using high resolution, accurate MS in conjunction with selective chemical reactivity, such as the unknown ion annotated with a characteristic m/z:RMT of 388.109:1.300.

FIG. 11 highlights the lead panel of 15 biomarkers of significance (FC>1.3; p<7 E-4, Bonferroni adjustment) in DBS extracts following supervised multivariate data analysis using partial least squares-discriminant analysis (PLS-DA) for data dimensionality reduction that differentiates asymptomatic CF infants from screen-negative/healthy controls shortly after birth, including 5 unknown ions of significance. Similarly, receiver operating characteristic (ROC) show a similar ranking for single metabolites, as well as improved performance for classifying CF infants from healthy controls when using metabolite ratiometric markers, such as nicotinamide/GSSG and L-histidine/unknown ion 310 m/z with excellent specificity and sensitivity (AUC >0.940). FIG. 12 shows a representative accurate MS/MS spectra following collisional-induced dissociation as required for identification of unknown ions, such as the divalent ion (M+2H$^{2+}$) associated with 388 m/z that is ascribed to a novel and previously unreported mixed glutathione disulfide based on its reactivity following chemical reduction.

EXAMPLE 3

Figure 13:
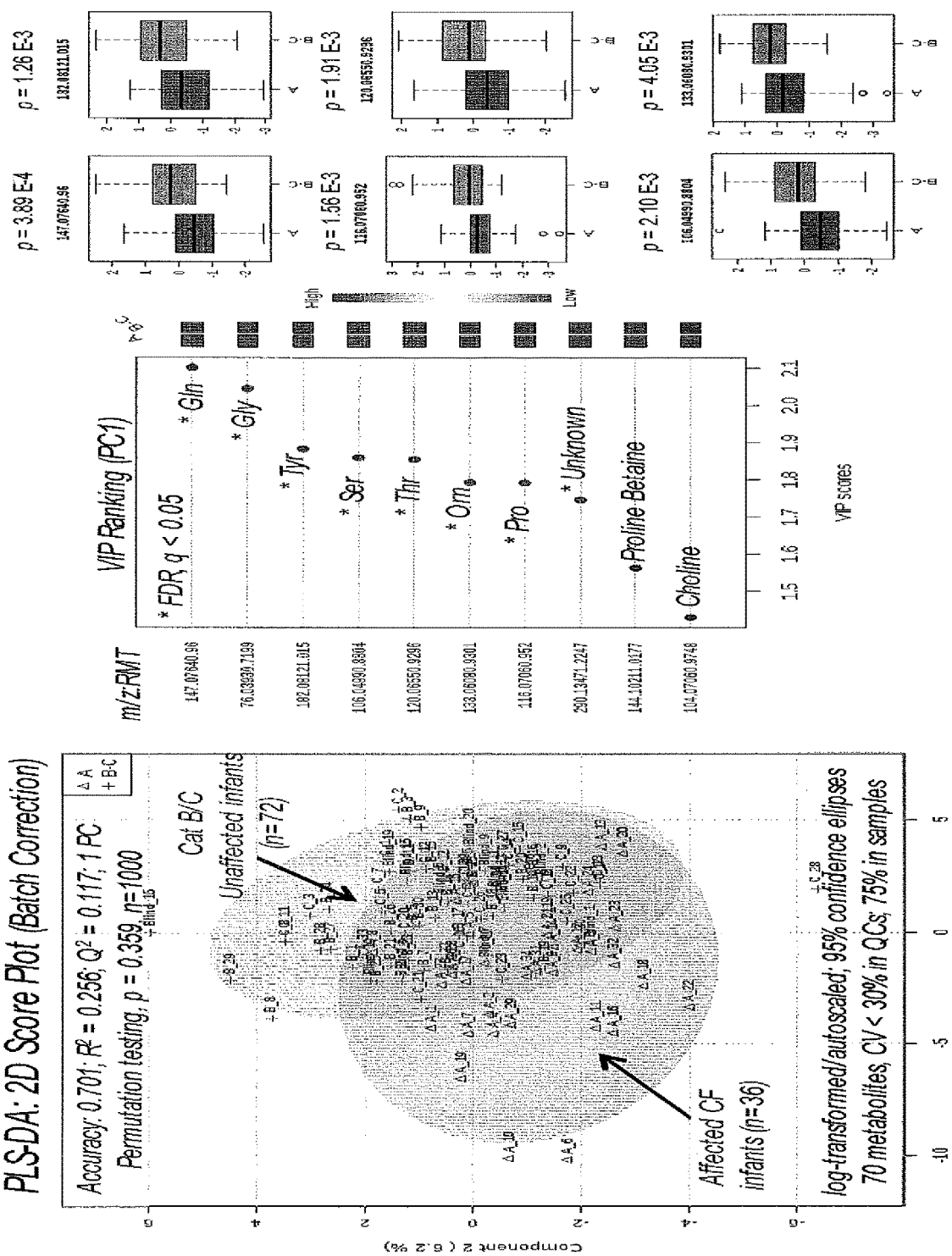
FIG. 13 depicts multivariate statistical analysis for classifying a panel of metabolites that are differentially expressed in affected/screen-positive CF newborn infants (n=36, category A) relative to two classes of unaffected/screen-positive controls, including infant carriers with a single disease causing CFTR mutation (n=37, category B) and infants with no known CFTR mutation (n=35, category C) based on 70 polar metabolites measured in retrospective dried blood spot (DBS) specimens by MSI-CE-MS, where (a) a 2D scores plot in partial-least squares discriminate analysis (PLS-DA) with biomarkers (metabolites with known and unknown chemical structures) annotated by their m/z:RMT using variable importance in projection (VIP) ranking, and (b) a 1-Way ANOVA/Fischer's LSD test.
Figure 13:
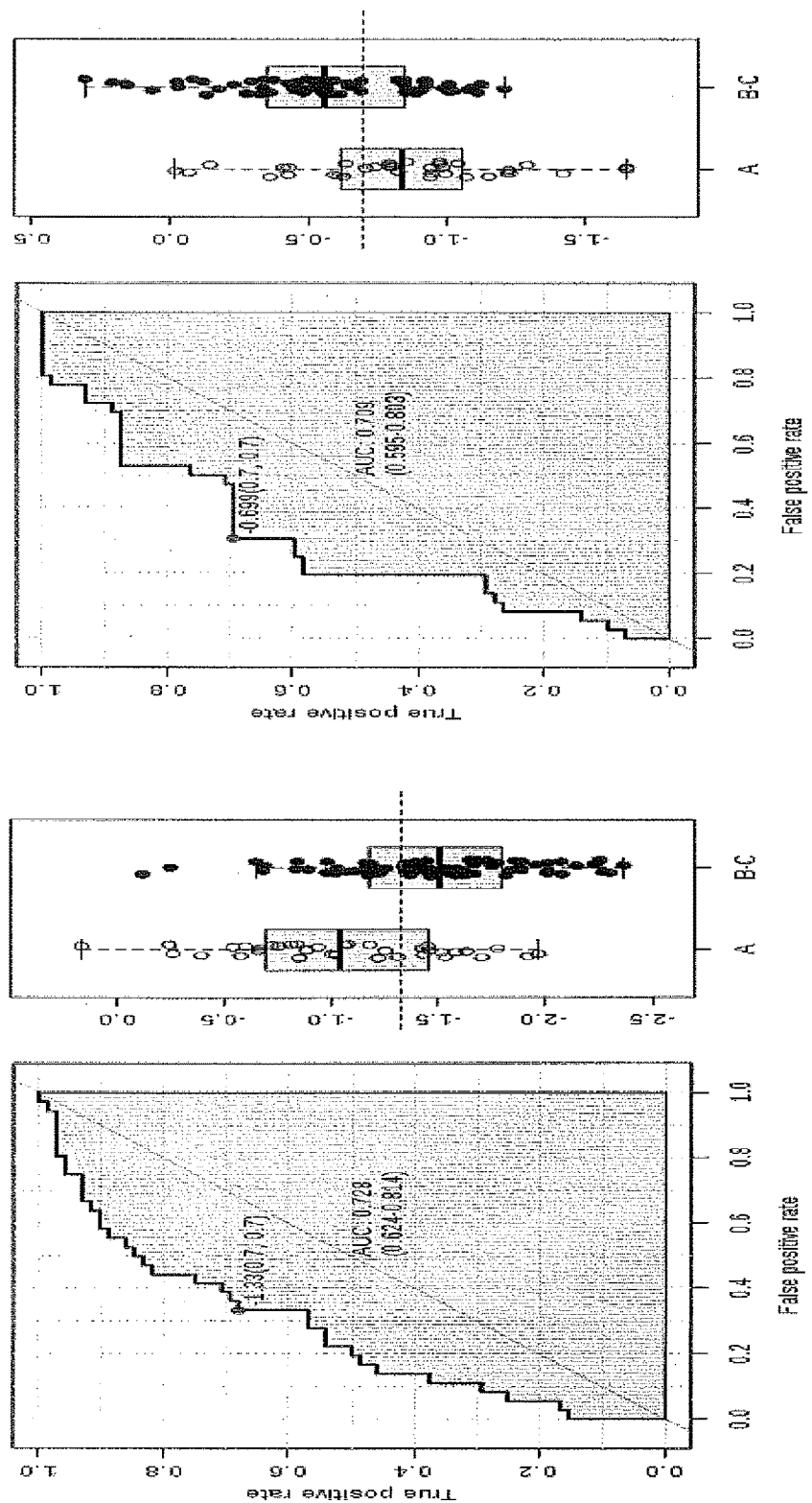
Figure 14:
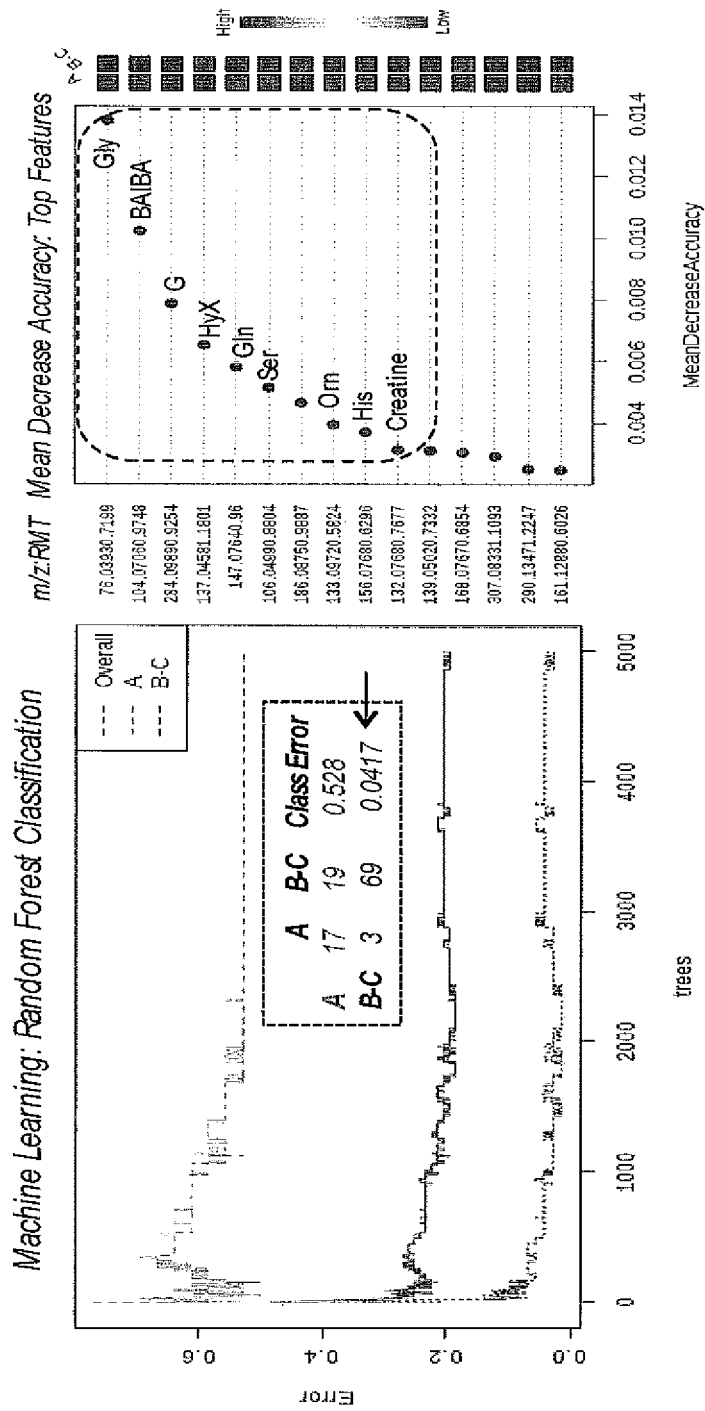
FIG. 14 depicts multivariate statistical analysis for classifying a panel of metabolites that are differentially expressed in affected/screen-positive CF newborn infants (n=36, category A) relative to unaffected/screen-positive controls (n=72, category B and C) from 70 polar metabolites measured in retrospective dried blood spot (DBS) specimens by MSI-CE-MS when using (a) a 2D scores plot in partial-least squares discriminate analysis (PLS-DA) with biomarkers annotated by their m/z:RMT using variable importance in projection (VIP) ranking and box plots highlighting the most significant metabolites in terms of average fold-change (FC) and statistical significance (p-value), as well as (b) receiver operating characteristic (ROC) curves for single or ratiometric CF-specific markers.

Identification of Biomarkers for Differential Screening of Authentic CF Infants From Screen-Positive/Unaffected Cases DBS extracts derived from affected CF infants relative to screen-positive CF cases (category B and C) who largely represent unaffected carriers with low sweat chloride results were further analyzed to determine biomarkers that can discriminate between affected and screen-positive CF infants since this addresses a major clinical problem related to the poor specificity of the conventional two-tiered IRT/mutation panel screen as a majority of screen-positive cases (80-85%) result in having low sweat chloride results (<30 mM);

A lead panel of 20 metabolites (and their ratios) were determined to be significantly different (FDR, q<0.05) in DBS extracts derived from affected CF infants relative to two groups of screen-positive/unaffected CF cases (category B and C) as determined by supervised multivariate data analysis using PLS-DA and ROC curves, as well as 1-way ANOVA/LSD tests (see FIG. 13). Indeed, several of the same metabolites that differentiate CF infants from healthy controls also discriminate authentic CF cases from screen-positive yet unaffected CF infants, including L-glutamine, L-glycine, L-tyrosine, L-serine, L-threonine, L-ornithine, L-proline, proline betaine, choline and an ion having a m/z:RMT ratio of 290.1347:0.2247, as well as ratiometric markers, such as nicotinamide/L-tyrosine. This data for the first time demonstrates the feasibility to stratify asymptomatic screen-positive CF infants with high IRT who are affected with CF from likely unaffected/carriers prior to genetic testing;

Similarly, FIG. 14 shows a lead panel of 7 metabolites from DBS were determined to be significantly different (FDR, q<0.05) in DBS extracts derived from affected CF infants relative to a single group of screen-positive/unaffected CF cases (category B and C) as determined by supervised multivariate data analysis using PLS-DA and ROC curves, as well as box plots using t-tests on log transformed/auto scaled data. This approach aims to identify predictive biomarkers that discriminate between affected CF and non-affected cases (carriers/false-positives) who have significantly elevated IRT results and a presumptive CF diagnosis. Indeed, the same metabolites that differentiate CF infants from both classes of non-affected CF infants (see FIG. 13) are also shown to be statistically significant here, including L-glutamine, glycine, L-tyrosine, L-serine, L-threonine, L-ornithine and an unknown metabolite, 290.135:1.225. Most of these metabolites can be readily measured via conventional direct infusion MS/MS infrastructure already available in newborn screening laboratories since they are used for multiplexed screening of dozens of amino acid, organic acid and fatty acid disorders, such as phenylketonuria.

Alternatively, FIG. 15 makes use of machine learning with random forests for classification of affected CF cases from unaffected carriers with low class error for screen-positive CF/unaffected infants of 4.2% based on all 70 metabolites used in the model. However, as shown by the mean decrease accuracy plot in FIG. 15 which ranks the most significant biomarkers associated with CF classification, the class error for distinguishing and potentially rejecting screen-positive yet unaffected carriers remains low even when using a smaller panel of 2 (Gly, BAIBA), 3 (Gly, BAIBA, G), 5 (Gly, BAIBA, G, HyX, Gln) or 10 (Gly, BAIBA, G, HyX, Gln, Ser, 186 m/z, Orn, His, Creatine) metabolites with errors of 18.1%, 15.3%, 12.5% and 9.7%, respectively. The following CF-specific markers were included in the panel list as determined by random forest classification in comparison to other univariate and multivariate statistical methods (e.g., Gly, Gln, Ser, Orn, His), and also including creatine, hypoxanthine, guanosine (G), beta-aminobutyric acid (BAIBA) and an ion (186.088:0.9887 m/z:RMT).

Thus, such a panel of CF-specific metabolites is useful to improve the specificity of the primary IRT screen (i.e., to confirm a presumptive diagnosis) thereby increasing the overall positive predictive value (PPV) of newborn screening of CF prior to genetic sequencing or follow-up confirmatory sweat testing. This use of such a metabolite screening panel will provide better health care savings by reducing the need for unnecessary sweat testing that causes undue parental anxiety due to the high rate of false-positives and unaffected carrier identification of the two-tiered screen.

EXAMPLE 4

Figure 16:
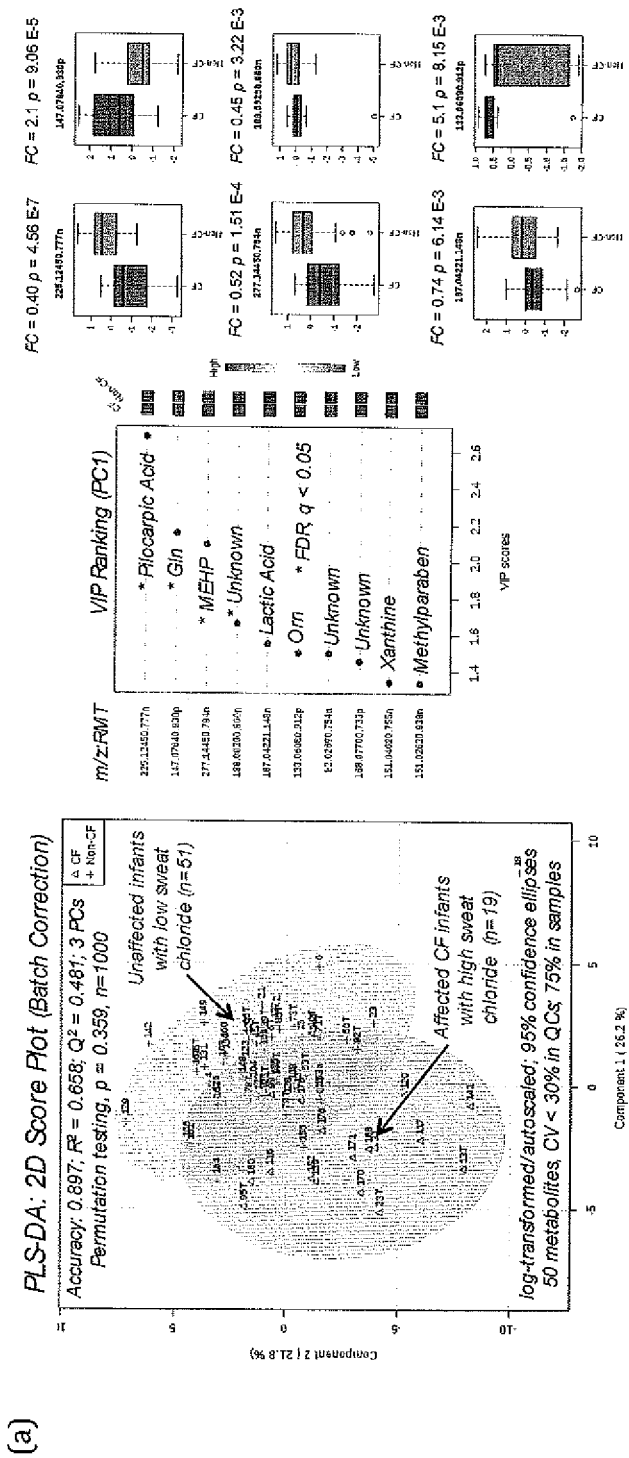
FIG. 16 depicts multivariate statistical analysis of 50 polar metabolites measured in pilocarpine-stimulated sweat specimens by MSI-CE-MS for the discovery of markers differentially expressed in affected infants with CF (n=19) relative to screen-positive/unaffected carriers (n=51) when using (a) a 2D scores plot in partial-least squares discriminate analysis (PLS-DA) with markers annotated by their variable importance in projection (VIP) ranking and (b) receiver operating characteristic (ROC) curves for ratiometric CF-specific markers in sweat.
Figure 16:
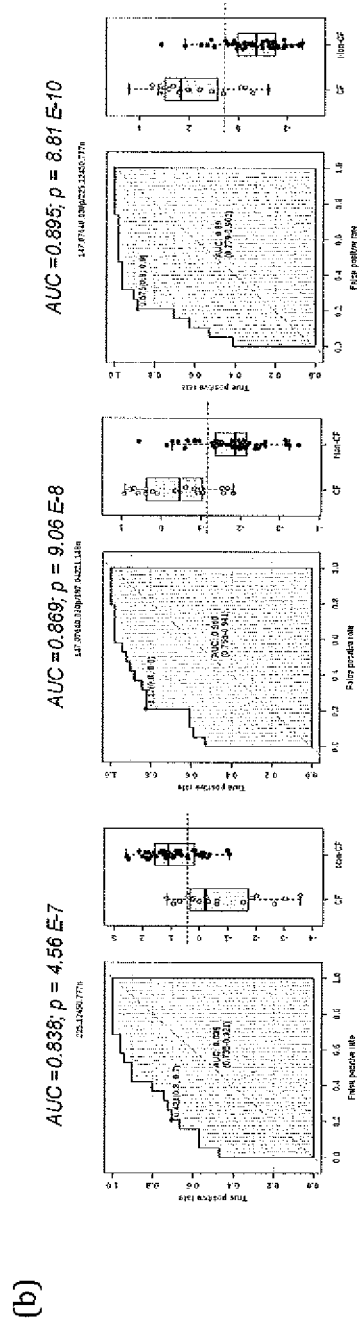
Figure 17:
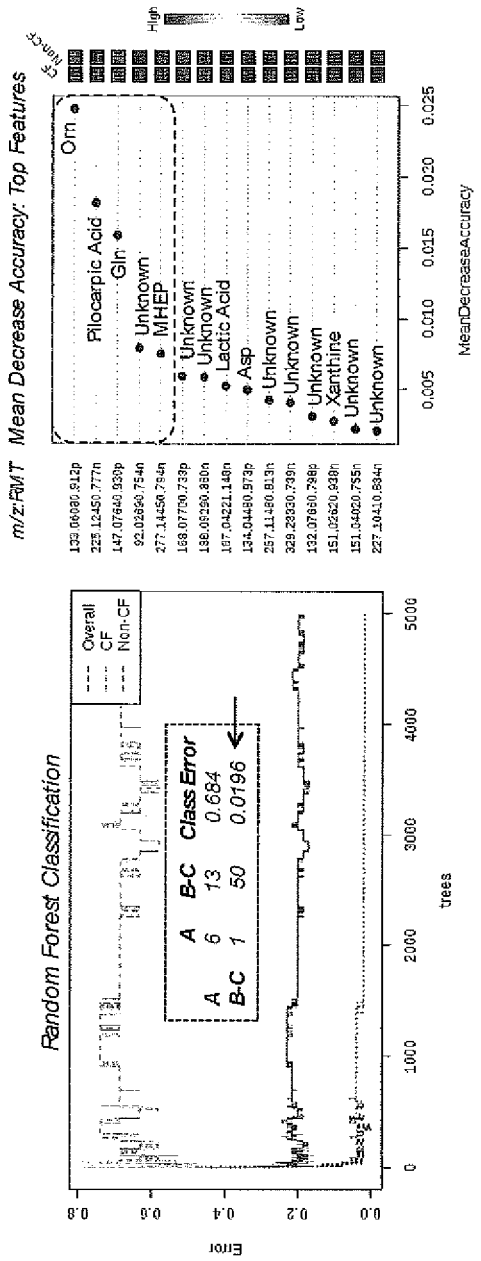
FIG. 17 depicts a machine learning algorithm based on random forests (RF) for classification of screen-positive/affected CF (category A with high sweat chloride >60 mM) from screen-positive/unaffected CF infants (category B/C with low sweat chloride <30 mM) based on 50 polar metabolites measured in retrospective sweat specimens by MSI-CE-MS, where (a) summarizes the predictive accuracy of the model notably for filtering unaffected CF infants (i.e., carriers/false-positives) with a low class error of 2.0% based on a panel of significant metabolites ranked by their mean decrease in accuracy, such as L-ornithine, pilocarpic acid, and L-glutamine.

Identification of Biomarkers in Sweat for Differential Diagnosis of Screen-Positive Infants Over 65 retrospective collected sweat specimens from screen-positive infants (1 mo) were analyzed and found to include 62 sweat-derived metabolites which were consistently measured in the majority of sweat samples when using MSI-CE-MS. Overall, pilocarpic acid (hydrolysis product of drug pilocarpine that is used to stimulate sweat from skin) remained as the most significant marker, which was significantly lower in sweat from authentic CF infants with high sweat chloride results as compared to screen-positive/unaffected carriers. In addition, other discriminatory markers of CF in sweat samples included, L-asparagine (Asn), L-glutamine (Gln), L-aspartic acid (Asp), L-ornithine (Orn), lactic acid, and an exogenous plasticizer hydrolysis product later confirmed to be monoethylhexylphthalic acid (MEHP), as well as five ions (m/z:RMT) of significance in sweat, including 168.077:0.733 (MH+, C₇H₉N₃O₂), 188.093:0.860 (M−H−, C₈H₁₅N O₄), 199.0725:0.868 (M−H−, C₈H₁₂N₂O₄), 213.099:0.635 (MH+, C₈H₁₂N₄O₃), and 163.0719:0.827 (MH+), as summarized in FIG. 16. Most of the ions appear to be dipeptides based on preliminary MS/MS spectral interpretation, whereas both pilocarpic acid and MEHP have been unambiguously identified by co-migration in CE followed by MS/MS spectral matches when comparing original ion measured in sweat from an authentic standard or spiked sweat run. FIG. 17 also shows that these same metabolites can be used as part of a panel to accurately classify affected CF infants from screen-positive/unaffected carriers when using machine learning with random forests with a class error rate under 2% for category BIC cases.

Overall, four top-ranked sweat metabolites were statistically significant after Bonferroni correction for multiple hypothesis testing, namely pilocarpic acid, Asn, MEHP and Gln. Unexpectedly, two of these putative biomarkers associated with CFTR dysfunction are exogenous/synthetic compounds likely differentially metabolized by a similar enzyme involved in their hydrolysis (i.e., esterases), such as human paraoxonase 1 [*Drug Metabol. Dispos.* 2011, 39:1345-52]. Interestingly, Gln has been found to be a discriminating biomarker characteristic of affected CF infants both in DBS extracts and sweat specimens based on this work.

The invention claimed is:

1. A method of diagnosing and treating cystic fibrosis or CFTR (cystic fibrosis transmembrane conductor regulator)-related metabolic syndrome in a human infant subject comprising:
   i) detecting in a biological sample from the subject a level of each metabolic biomarker including L-glutamine (Gln), L-tyrosine (Tyr), L-serine, glycine and a metabolite having a m/z of 290.1347 and RMT of 1.2247, and/or L-glutamine, pilocarpic acid and mono(2-ethylhexyl)phthalate (MEHP);
   ii) comparing the level of each of the biomarkers to a corresponding control level for each biomarker;
   iii) determining that the infant subject has cystic fibrosis when the levels of L-glutamine, glycine, L-serine, L-tyrosine and a metabolite having a m/z of 290.1347 and RMT of 1.2247 are statistically significantly reduced from their corresponding control levels when the sample is a blood, serum or plasma sample, and/or the level of L-glutamine is increased, and the levels of MEHP and pilocarpic acid are reduced, in comparison to their corresponding control levels when the sample is a sweat sample;
   iv) treating the infant subject determined to have cystic fibrosis with one or more of nutritional supplementation, a CFTR potentiator, a CFTR corrector, an antibiotic, an anti-inflammatory agent, a mucus-thinning drug, a bronchodilator and a pancreatic enzyme.

2. The method of claim 1, wherein the biological sample is a blood, serum or plasma sample, and the levels of each of the biomarkers L-glutamine, glycine, L-serine, L-tyrosine and a metabolite having a m/z of 290.1347 and RMT of 1.2247 are reduced in comparison to their corresponding control levels.

3. The method of claim 2, wherein the sample is a dried blood sample.

4. The method of claim 2, wherein biomarkers, L-threonine and L-ornithine, are additionally detected, and reduced levels of L-threonine and L-ornithine in comparison to their corresponding control levels are indicative of CF in the infant.

5. The method of claim 1, comprising an additional step of determining a ratio of the levels of two biomarkers, comparing the ratio to a corresponding control ratio, determining the difference between the ratio and the corresponding control ratio, and determining that the subject has cystic fibrosis when the difference in the ratio is statistically different from the corresponding control ratio.

6. The method of claim 1, wherein the corresponding control level is the level of the biomarker in a sample from a healthy infant or healthy infant population that do not have cystic fibrosis.

7. The method of claim 1, wherein the corresponding control level is the level of the biomarker in a sample or samples from one or more infants that are carriers that do not have cystic fibrosis.

8. The method of claim 1, wherein the detection of the level of one or more biomarkers is by a mass spectrometry (MS)-based method selected from direct infusion-mass spectrometry, electrospray ionization (ESI)-MS, desorption electrospray ionization (DESI)-MS, direct analysis in real-time (DART)-MS, atmospheric pressure chemical ionization (APCI)-MS, liquid chromatography-mass spectrometry (LC-MS), gas chromatography- mass spectrometry (GC-MS), or capillary electrophoresis-mass spectrometry (CE-MS).

9. The method of claim 1, wherein the biological sample is a sweat sample and the level of L-glutamine is increased, and the levels of MEHP and pilocarpic acid are reduced, in comparison to their corresponding control levels.

10. A method of confirming that a human infant subject is affected with cystic fibrosis and treating the subject for cystic fibrosis comprising the steps of: i) detecting in a biological sample from the subject a level of each metabolic biomarker including L-glutamine (Gln), L-tyrosine (Tyr), L-serine (Ser), glycine and a metabolite having a m/z:RMT of 290.1347:12247, or L-glutamine, pilocarpic acid and MEHP; ii) comparing the level of each of the biomarkers to a corresponding control level for each biomarker, and iii) confirming that the infant subject has cystic fibrosis when the levels of L-glutamine, glycine, L-serine, L-tyrosine and a metabolite having a m/z of 290.1347 and RMT of 1.2247 are reduced in comparison to their corresponding control levels in a blood, serum or plasma sample, or the level of L-glutamine is increased, and the levels of MEHP and pilocarpic acid are reduced, in comparison to their corresponding control levels in a sweat sample and treating the infant subject with one or more of a CFTR potentiator, a CFTR corrector, an antibiotic, an anti-inflammatory agent, a mucus-thinning drug, a bronchodilator and a pancreatic enzyme.

11. The method of claim 10, wherein the biological sample is a blood, serum or plasma sample, and the levels of each of the biomarkers L-glutamine, glycine, L-serine, L-tyrosine and a metabolite having a m/z:RMT of 290.1347:12247 are reduced in comparison to their corresponding control levels.

12. The method of claim 11, wherein the sample is a dried blood sample.

13. The method of claim 11, wherein biomarkers, L-threonine and L-ornithine, are additionally detected, and reduced levels of L-threonine and L-ornithine in comparison to their corresponding control levels are indicative of CF in the infant.

14. The method of claim 10, wherein the biological sample is a sweat sample and the level of L-glutamine is increased and the levels of MEHP and pilocarpic acid are reduced in comparison to their corresponding control levels.

\* \* \* \* \*